(12) United States Patent
Jockers et al.

(10) Patent No.: US 7,211,399 B2
(45) Date of Patent: May 1, 2007

(54) METHOD FOR DETECTING LEPTIN RECEPTOR LIGANDS

(75) Inventors: Ralf Jockers, Bures sur Yvette (FR); Cyril Couturier, Paris (FR)

(73) Assignees: Aventis Pharma S.A., Paris (FR); CNRS, Paris (FR); INSERM, Paris (FR)

( * ) Notice: Subject to any disclaimer, the term of this patent is extended or adjusted under 35 U.S.C. 154(b) by 554 days.

(21) Appl. No.: 10/373,624

(22) Filed: Feb. 25, 2003

(65) Prior Publication Data

US 2004/0132093 A1 Jul. 8, 2004

(30) Foreign Application Priority Data

Feb. 26, 2002 (FR) .................................. 02 02431

(51) Int. Cl.
*G01N 33/53* (2006.01)
*C12Q 1/66* (2006.01)
*C07K 1/00* (2006.01)
*C07H 21/04* (2006.01)
*C12P 21/04* (2006.01)

(52) U.S. Cl. .......................... 435/7.1; 435/8; 435/69.7; 435/69.1; 530/350; 536/23.4; 536/23.5

(58) Field of Classification Search ..................... None
See application file for complete search history.

(56) References Cited

FOREIGN PATENT DOCUMENTS

EP          0187519       7/1985
WO      WO 97/19952       6/1997
WO      WO 99/66324      12/1999

OTHER PUBLICATIONS

Wells, 1990. Biochemistry 29:8509-8517.*
Ngo et al. 1994. in The Protein Folding Problem and Tertiary Structure Prediction pp. 492-495.*
Kopelman, 2000. Nature 404:635-643.*
Chicurel 2000. Nature 404:538-540.*
Lee et al. 2002. European Journal of Pharm. 440:129-139.*
Salvador et al. 2001. Expert Opin Pharmacother. 2:1615-1622.*
Cock et al. 2003. Lancet 362:1572-1574.*
A. Lundin et al., Expression and Intracellular localization of leptin receptor long isoform-GFP chimera, Biochimica et Biophysica Acta 1499, 2000, pp. 130-138.
B.A. Pollok et al., Using GFP in FRET-based applications, Trends in Cell Biology, vol. 9, Feb. 1999, pp. 57-60.
D.C. Prasher et al., Primary structure of the *Aequorea victoria* green-fluorescent protein, Gene, vol. 111, 1992, pp. 229-233.
G. Lee et al., Abnormal splicing of the leptin receptor in diabetic mice, Nature, vol. 379, Feb. 15, 1996, pp. 632-635.
J.R. Blinks et al., Photoproteins as Biological Calcium Indicators, Pharmacological Reviews, vol. 28, No. 1, 1976, pp. 1-93.
K. Clement et al., A mutation in the human leptin receptor gene causes obesity and pituitary dysfunction, Nature, vol. 392, Mar. 26, 1998, pp. 398-401.

K.M. Kroger et al., Constitutive and Agonist-dependent Homo-oligomerization of the Thyrotropin-releasing Hormone Receptor. Journ of Biological Chemistry, vol. 276, No. 16, Apr. 20, 2001, pp. 12736-12743.
L. Matyus, Fluorescence resonance energy transfer measurements on cell surfaces. A spectroscopic tool for deterimining protein interactions. J. Photochem. Photobiol. vol. 12, 1992, pp. 323-337.
L.A. Tartaglia, The Leptin Receptor, Journ. of Bio. Chem., vol. 272, No. 10, Mar. 7, 1997, pp. 6093-6096.
M.V. Matz et al., Fluorescent proteins from nonbioluminescent Anthozoe species, Nature Biotechnology, vol. 17, Oct. 1999, pp. 969-973.
N. Boute et al., Monitoring the Activation State of the Insulin Receptor Using Bioluminescence Resonance Energy Transfer, Molecular Pharmacology, vol. 60, No. 4, 2001, pp. 640-645.
O. Gavrilova et al., Hyperleptinemia of Pregnancy Associated with the Appearance of a Circulating Form of the Leptin Receptor, Journ. of Biological Chemistry, vol. 272, No. 48, Nov. 28, 1997, pp. 30546-30551.
R.Y. Tsein, The Green Fluorescent Protein, Annu. Rev. Biochem, vol. 67, 1998, pp. 509-544.
S. Angers et al., Detection of Beta2-adrenergic receptor dimerization in living cells using bioluminescence resonance energy transfer (BRET), PNAS, vol. 97, No. 7, Mar. 28, 2000, pp. 3684-3689.
S. Inouye et al., Cloning and sequence analysis of cDNA for the luminescent protein aequorin, PNAS, USA, vol. 82, May 1985, pp. 3154-3158.
T.R. Flotte et al., Gene Expression from Adeno-associated Virus Vectors in Airway Epithelial Cells, Am. J. Respir. Cell Mol. Biol., vol. 7, 1992, pp. 349-356.
V. Baubet et al., Chimeric green fluorescent protein-aequorin as biolumuneescent Ca2+ reporter at the single-cell level, PNAS, vol. 97, No. 13, Jun. 20, 2000, pp. 7260-7265.
W.W. Lorenz et al., Isolation and expression of a cDNA encoding *Renilla reniformis* luciferase, PNAS, USA, vol. 88, May 1991, pp. 4438-4442.
Y. Wang et al., A study of protein—protein interactions in living cells using luminescence resonance energy transfer (LRET) from *Renilla* luciferase to Aequorea GFP, Mol. Gen. Genet, vol. 264, 2001, pp. 578-587.
Y. Xu et al., A bioluminescence resonance energy transfer (BRET) system: Application to interacting circadian clock proteins, Proc. Natl. Acad. Sci. USA, Cell Biology, vol. 96, Jan. 1999, pp. 151-156.

(Continued)

*Primary Examiner*—Janet L. Andres
*Assistant Examiner*—Shulamitah H. Shafer
(74) *Attorney, Agent, or Firm*—Karen I. Krupen

(57) ABSTRACT

The present invention relates to a method for detecting leptin receptor ligands using resonance energy transfer between fusion proteins comprising a leptin receptor and energy donor protein and a leptin receptor and energy acceptor protein. The present invention also relates to the fusion proteins for implementing said method.

10 Claims, 6 Drawing Sheets

OTHER PUBLICATIONS

Z. Cheng et al., Agonist-dependent Dissociation of Oligomeric Complexes of G Protein-coupled Cholecystokinin Receptors Demonstrated in Living Cells Using Bioluminescence Resonance Energy Transfer, Journ. of Biological Chemistry, vol. 276, No. 51, Dec. 21, 2001, pp. 48040-48047.

M. Maamra et al., Generation of Human Soluble Leptin Receptor by Proteolytic Cleavage of Membrane-Anchored Recepors, Endocrinology, vol. 142, 2001, pp. 4389-4393.

* cited by examiner

SEQUENCE LISTING

<160> NUMBER OF SEQ ID NOS: 8

<210> SEQ ID NO 1
<211> LENGTH: 2691
<212> TYPE: DNA
<213> ORGANISM: homo sapiens

<400> SEQUENCE: 1

```
atgatttgtc aaaaattctg tgtggttttg ttacattggg aatttattta tgtgataact      60
gcgtttaact tgtcatatcc aattactcct tggagattta agttgtcttg catgccacca     120
```

-continued

```
aattcaacct atgactactt ccttttgcct gctggactct caaagaatac ttcaaattcg    180
aatggacatt atgagacagc tgttgaacct aagtttaatt caagtggtac tcactttct     240 aacttatcca aaacaacttt ccactgttgc tttcggagtg agcaagatag aaactgctcc    300
ttatgtgcag acaacattga aggaaagaca tttgtttcaa cagtaaattc tttagttttt    360
caacaaatag atgcaaactg gaacatacag tgctggctaa aaggagactt aaaattattc    420
atctgttatg tggagtcatt atttaagaat ctattcagga attataacta aaggtccat     480 cttttatatg ttctgcctga agtgttagaa gattcacctc tggttcccca aaaaggcagt    540
tttcagatgg ttcactgcaa ttgcagtgtt catgaatgtt gtgaatgtct tgtgcctgtg    600
ccaacagcca aactcaacga cactctcctt atgtgtttga aaatcacatc tggtggagta    660
attttccagt cacctctaat gtcagttcag cccataaata tggtgaagcc tgatccacca    720
ttaggtttgc atatggaaat cacagatgat ggtaatttaa agatttcttg gtccagccca    780
ccattggtac catttccact tcaatatcaa gtgaaatatt cagagaattc tacaacagtt    840
atcagagaag ctgacaagat tgtctcagct acatccctgc tagtagacag tatacttcct    900
gggtcttcgt atgaggttca ggtgaggggc aagagactgg atgcccagg aatctggagt     960 gactggagta ctcctcgtgt ctttaccaca caagatgtca tatactttcc acctaaaatt    1020
ctgacaagtt tgggtctaa tgtttctttt cactgcatct ataagaagga aaacaagatt     1080
gttccctcaa aagagattgt ttggtggatg aatttagctg agaaaattcc tcaaagccag    1140
tatgatgttg tgagtgatca tgttagcaaa gttactttt tcaatctgaa tgaaaccaaa     1200
cctcgaggaa agtttaccta tgatgcagtg tactgctgca atgaacatga atgccatcat    1260
cgctatgctg aattatatgt gattgatgtc aatatcaata tctcatgtga aactgatggg    1320
tacttaacta aaatgacttg cagatggtca accagtacaa tccagtcact tgcggaaagc    1380
actttgcaat tgaggtatca taggagcagc ctttactgtt ctgatattcc atctattcat    1440
cccatatctg agcccaaaga ttgctatttg cagagtgatg ttttttatga atgcatttt     1500 cagccaatct tcctattatc tggctacaca atgtggatta ggatcaatca ctctctaggt    1560
tcacttgact ctccaccaac atgtgtcctt cctgattctg tggtgaagcc actgcctcca    1620
tccagtgtga aagcagaaat tactataaac attggattat tgaaaatatc ttgggaaaag    1680
ccagtctttc cagagaataa ccttcaattc cagattcgct atggtttaag tggaaaagaa    1740
gtacaatgga agatgtatga ggtttatgat gcaaaatcaa aatctgtcag tctcccagtt    1800
ccagacttgt gtgcagtcta tgctgttcag gtgcgctgta gaggctaga tggactggga    1860 tattggagta attggagcaa tccagcctac acagttgtca tggatataaa agttcctatg    1920
agaggacctg aattttggag aataattaat ggagatacta tgaaaaagga gaaaaatgtc    1980
actttacttt ggaagcccct gatgaaaaat gactcattgt gcagtgttca gagatatgtg    2040
ataaaccatc atacttcctg caatggaaca tggtcagaag atgtgggaaa tcacacgaaa    2100
ttcactttcc tgtggacaga gcaagcacat actgttacgg ttctggccat caattcaatt    2160
ggtgcttctg ttgcaaattt taatttaacc ttttcatggc ctatgagcaa agtaaatatc    2220
gtgcagtcac tcagtgctta tccttaaac agcagttgtg tgattgttc ctggatacta      2280 tcacccagtg attacaagct aatgtatttt attattgagt ggaaaaatct taatgaagat    2340
ggtgaaataa aatggcttag aatctcttca tctgttaaga agtattatat ccatgatcat    2400
tttatcccca ttgagaagta ccagttcagt ctttacccaa tatttatgga aggagtggga    2460
aaaccaaaga taattaatag tttcactcaa gatgatattg aaaaacacca gagtgatgca    2520
```

```
ggtttatatg taattgtgcc agtaattatt tcctcttcca tcttattgct tggaacatta    2580
ttaatatcac accaaagaat gaaaaagcta ttttgggaag atgttccgaa ccccaagaat    2640
tgttcctggg cacaaggact taattttcag aagagaacgg acattctttg a             2691
```

<210> SEQ ID NO 2
<211> LENGTH: 896
<212> TYPE: PRT
<213> ORGANISM: homo sapiens

<400> SEQUENCE: 2

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
```

-continued

```
              340                 345                 350
Ile Tyr Lys Lys Glu Asn Lys Ile Val Pro Ser Lys Glu Ile Val Trp
            355                 360                 365
Trp Met Asn Leu Ala Glu Lys Ile Pro Gln Ser Gln Tyr Asp Val Val
        370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
            420                 425                 430
Asn Ile Ser Cys Glu Thr Asp Gly Tyr Leu Thr Lys Met Thr Cys Arg
        435                 440                 445
Trp Ser Thr Ser Thr Ile Gln Ser Leu Ala Glu Ser Thr Leu Gln Leu
    450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
            500                 505                 510
Ile Arg Ile Asn His Ser Leu Gly Ser Leu Asp Ser Pro Pro Thr Cys
        515                 520                 525
Val Leu Pro Asp Ser Val Val Lys Pro Leu Pro Pro Ser Ser Val Lys
    530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
            580                 585                 590
Ser Lys Ser Val Ser Leu Pro Val Pro Asp Leu Cys Ala Val Tyr Ala
        595                 600                 605
Val Gln Val Arg Cys Lys Arg Leu Asp Gly Leu Gly Tyr Trp Ser Asn
    610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
            660                 665                 670
Leu Cys Ser Val Gln Arg Tyr Val Ile Asn His His Thr Ser Cys Asn
        675                 680                 685
Gly Thr Trp Ser Glu Asp Val Gly Asn His Thr Lys Phe Thr Phe Leu
    690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                725                 730                 735
Lys Val Asn Ile Val Gln Ser Leu Ser Ala Tyr Pro Leu Asn Ser Ser
            740                 745                 750
Cys Val Ile Val Ser Trp Ile Leu Ser Pro Ser Asp Tyr Lys Leu Met
        755                 760                 765
```

```
Tyr Phe Ile Ile Glu Trp Lys Asn Leu Asn Glu Asp Gly Glu Ile Lys
770                 775                 780
Trp Leu Arg Ile Ser Ser Val Lys Tyr Tyr Ile His Asp His
785                 790                 795                 800
Phe Ile Pro Ile Glu Lys Tyr Gln Phe Ser Leu Tyr Pro Ile Phe Met
                805                 810                 815
Glu Gly Val Gly Lys Pro Lys Ile Ile Asn Ser Phe Thr Gln Asp Asp
                820                 825                 830
Ile Glu Lys His Gln Ser Asp Ala Gly Leu Tyr Val Ile Val Pro Val
                835                 840                 845
Ile Ile Ser Ser Ser Ile Leu Leu Leu Gly Thr Leu Leu Ile Ser His
            850                 855                 860
Gln Arg Met Lys Lys Leu Phe Trp Glu Asp Val Pro Asn Pro Lys Asn
865                 870                 875                 880
Cys Ser Trp Ala Gln Gly Leu Asn Phe Gln Lys Arg Thr Asp Ile Leu
                885                 890                 895
```

<210> SEQ ID NO 3
<211> LENGTH: 2751
<212> TYPE: DNA
<213> ORGANISM: Artificial
<220> FEATURE:
<223> OTHER INFORMATION: fusion protein comprising a portion of OBRs

<400> SEQUENCE: 3

```
atggttcttg ccagctctac caccagcatc acaccatgc tgctcctgct cctgatgctc      60
ttccacctgg gactccaagc ttcaatctcg gcgcgccagg agcagaagct tatctcggag     120
gaggacctga cgcgttatcc aattactcct tggagattta gttgtcttg catgccacca      180
aattcaacct atgactactt cctttgcct gctggactct caaagaatac ttcaaattcg     240
aatggacatt atgagacagc tgttgaacct aagtttaatt caagtggtac tcacttttct     300
aacttatcca aacaactttt ccactgttgc tttcggagtg agcaagatag aaactgctcc     360
ttatgtgcag acaacattga aggaacgaca tttgttttcaa cagtaaattc tttagttttt     420
caacaaatag atgcaaactg aacatacag tgctggctaa aaggagactt aaaattattc     480
atctgttatg tggagtcatt atttaagaat ctattcagga attataacta aaggtccat      540
ctttatatg ttctgcctga agtgttagaa gattcacctc tggttcccca aaaaggcagt     600
tttcagatgg ttcactgcaa ttgcagtgtt catgaatgtt gtgaatgtct tgtgcctgtg     660
ccaacagcca aactcaacga cactctcctt atgtgtttga aaatcacatc tggtggagta     720
atttttccggt cacctctaat gtcagttcag cccataaata tggtgaagcc tgatccacca     780
ttaggtttgc atatggaaat cacagatgat ggtaatttaa agatttcttg gtccagccca     840
ccattggtac catttccact tcaatatcaa gtgaaatatt cagagaattc tacaacagtt     900
atcagagaag ctgacaagat tgtctcagct acatccctgc tagtagacag tatacttcct     960
gggtcttcgt atgaggttca ggtgaggggc aagagactgg atggcccagg aatctggagt    1020
gactggagta ctcctcgtgt ctttaccaca caagatgtca tatactttcc acctaaaatt    1080
ctgacaagtg ttgggtctaa tgtttctttt cactgcatct ataagaagga aaacaagatt    1140
gttccctcaa aagagattgt tggtggatg aatttagctg agaaattcc tcaaagccag    1200
tatgatgttg tgagtgatca tgttagcaaa gttacttttt tcaatctgaa tgaaaccaaa    1260
cctcgaggaa agtttaccta tgatgcagtg tactgctgca tgaacatga atgccatcat    1320
```

```
cgctatgctg aattatatgt gattgatgtc aatatcaata tctcatgtga aactgatggg   1380
tacttaacta aaatgacttg cagatggtca accagtacaa tccagtcact tgcggaaagc   1440
actttgcaat tgaggtatca taggagcagc ctttactgtt ctgatattcc atctattcat   1500
cccatatctg agcccaaaga ttgctatttg cagagtgatg gttttatga atgcattttc    1560 cagccaatct tcctattatc tggctacaca atgtggatta ggatcaatca ctctctaggt   1620
tcacttgact ctccaccaac atgtgtcctt cctgattctg tggtgaagcc actgcctcca   1680
tccagtgtga aagcagaaat tactataaac attggattat tgaaaatatc ttgggaaaag   1740
ccagtctttc cagagaataa ccttcaattc cagattcgct atggtttaag tggaaaagaa   1800
gtacaatgga agatgtatga ggtttatgat gcaaaatcaa aatctgtcag tctcccagtt   1860
ccagacttgt gtgcagtcta tgctgttcag gtgcgctgta agaggctaga tggactggga   1920
tattggagta attggagcaa tccagcctac acagttgtca tggatataaa agttcctatg   1980
agaggacctg aattttggag aataattaat ggagatacta tgaaaaagga aaaaatgtc    2040 actttacttt ggaagcccct gatgaaaaat gactcattgt gcagtgttca gagatatgtg   2100
ataaaccatc atacttcctg caatggaaca tggtcagaag atgtgggaaa tcacacgaaa   2160
ttcactttcc tgtggacaga gcaagcacat actgttacgg ttctggccat caattcaatt   2220
ggtgcttctg ttgcaaattt taatttaacc ttttcatggc ctatgagcaa agtaaatatc   2280
gtgcagtcac tcagtgctta tcctttaaac agcagttgtg tgattgtttc ctggatacta   2340
tcacccagtg attacaagct aatgtatttt attattgagt ggaaaaatct taatgaagat   2400
ggtgaaataa aatggcttag aatctcttca tctgttaaga agtattatat ccatgatcat   2460
tttatcccca ttgagaagta ccagttcagt ctttacccaa tatttatgga aggagtggga   2520
aaaccaaaga taattaatag tttcactcaa gatgatattg aaaaacacca gagtgatgca   2580
ggtttatatg taattgtgcc agtaattatt tcctcttcca tcttattgct tggaacatta   2640
ttaatatcac accaaagaat gaaaaagcta ttttgggaag atgttccgaa ccccaagaat   2700
tgttcctggg cacaaggact taattttcag aagagaacgg acattctttg a            2751
```

<210> SEQ ID NO 4
<211> LENGTH: 916
<212> TYPE: PRT
<213> ORGANISM: Artificial
<220> FEATURE:
<223> OTHER INFORMATION: fusion protein comprising a portion of OBRs

<400> SEQUENCE: 4

```
Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
                20                  25                  30

Gln Glu Gln Lys Leu Ile Ser Glu Glu Asp Leu Thr Arg Tyr Pro Ile
            35                  40                  45

Thr Pro Trp Arg Phe Lys Leu Ser Cys Met Pro Pro Asn Ser Thr Tyr
        50                  55                  60

Asp Tyr Phe Leu Leu Pro Ala Gly Leu Ser Lys Asn Thr Ser Asn Ser
65                  70                  75                  80

Asn Gly His Tyr Glu Thr Ala Val Glu Pro Lys Phe Asn Ser Ser Gly
                85                  90                  95

Thr His Phe Ser Asn Leu Ser Lys Thr Thr Phe His Cys Cys Phe Arg
            100                 105                 110
```

-continued

```
Ser Glu Gln Asp Arg Asn Cys Ser Leu Cys Ala Asp Asn Ile Glu Gly
        115                 120                 125

Thr Thr Phe Val Ser Thr Val Asn Ser Leu Val Phe Gln Gln Ile Asp
130                 135                 140

Ala Asn Trp Asn Ile Gln Cys Trp Leu Lys Gly Asp Leu Lys Leu Phe
145                 150                 155                 160

Ile Cys Tyr Val Glu Ser Leu Phe Lys Asn Leu Phe Arg Asn Tyr Asn
                165                 170                 175

Tyr Lys Val His Leu Leu Tyr Val Leu Pro Glu Val Leu Glu Asp Ser
                180                 185                 190

Pro Leu Val Pro Gln Lys Gly Ser Phe Gln Met Val His Cys Asn Cys
            195                 200                 205

Ser Val His Glu Cys Cys Glu Cys Leu Val Pro Val Pro Thr Ala Lys
        210                 215                 220

Leu Asn Asp Thr Leu Leu Met Cys Leu Lys Ile Thr Ser Gly Gly Val
225                 230                 235                 240

Ile Phe Arg Ser Pro Leu Met Ser Val Gln Pro Ile Asn Met Val Lys
                245                 250                 255

Pro Asp Pro Pro Leu Gly Leu His Met Glu Ile Thr Asp Asp Gly Asn
            260                 265                 270

Leu Lys Ile Ser Trp Ser Ser Pro Pro Leu Val Pro Phe Pro Leu Gln
        275                 280                 285

Tyr Gln Val Lys Tyr Ser Glu Asn Ser Thr Thr Val Ile Arg Glu Ala
    290                 295                 300

Asp Lys Ile Val Ser Ala Thr Ser Leu Leu Val Asp Ser Ile Leu Pro
305                 310                 315                 320

Gly Ser Ser Tyr Glu Val Gln Val Arg Gly Lys Arg Leu Asp Gly Pro
                325                 330                 335

Gly Ile Trp Ser Asp Trp Ser Thr Pro Arg Val Phe Thr Thr Gln Asp
            340                 345                 350

Val Ile Tyr Phe Pro Pro Lys Ile Leu Thr Ser Val Gly Ser Asn Val
        355                 360                 365

Ser Phe His Cys Ile Tyr Lys Lys Glu Asn Lys Ile Val Pro Ser Lys
    370                 375                 380

Glu Ile Val Trp Trp Met Asn Leu Ala Glu Lys Ile Pro Gln Ser Gln
385                 390                 395                 400

Tyr Asp Val Val Ser Asp His Val Ser Lys Val Thr Phe Phe Asn Leu
                405                 410                 415

Asn Glu Thr Lys Pro Arg Gly Lys Phe Thr Tyr Asp Ala Val Tyr Cys
            420                 425                 430

Cys Asn Glu His Glu Cys His His Arg Tyr Ala Glu Leu Tyr Val Ile
        435                 440                 445

Asp Val Asn Ile Asn Ile Ser Cys Glu Thr Asp Gly Tyr Leu Thr Lys
450                 455                 460

Met Thr Cys Arg Trp Ser Thr Ser Thr Ile Gln Ser Leu Ala Glu Ser
465                 470                 475                 480

Thr Leu Gln Leu Arg Tyr His Arg Ser Ser Leu Tyr Cys Ser Asp Ile
                485                 490                 495

Pro Ser Ile His Pro Ile Ser Glu Pro Lys Asp Cys Tyr Leu Gln Ser
            500                 505                 510

Asp Gly Phe Tyr Glu Cys Ile Phe Gln Pro Ile Phe Leu Leu Ser Gly
        515                 520                 525

Tyr Thr Met Trp Ile Arg Ile Asn His Ser Leu Gly Ser Leu Asp Ser
```

```
            530                 535                 540
Pro Pro Thr Cys Val Leu Pro Asp Ser Val Val Lys Pro Leu Pro Pro
545                 550                 555                 560

Ser Ser Val Lys Ala Glu Ile Thr Ile Asn Ile Gly Leu Leu Lys Ile
                565                 570                 575

Ser Trp Glu Lys Pro Val Phe Pro Glu Asn Asn Leu Gln Phe Gln Ile
                580                 585                 590

Arg Tyr Gly Leu Ser Gly Lys Glu Val Gln Trp Lys Met Tyr Glu Val
                595                 600                 605

Tyr Asp Ala Lys Ser Lys Ser Val Ser Leu Pro Val Pro Asp Leu Cys
610                 615                 620

Ala Val Tyr Ala Val Gln Val Arg Cys Lys Arg Leu Asp Gly Leu Gly
625                 630                 635                 640

Tyr Trp Ser Asn Trp Ser Asn Pro Ala Tyr Thr Val Val Met Asp Ile
                645                 650                 655

Lys Val Pro Met Arg Gly Pro Glu Phe Trp Arg Ile Ile Asn Gly Asp
                660                 665                 670

Thr Met Lys Lys Glu Lys Asn Val Thr Leu Leu Trp Lys Pro Leu Met
                675                 680                 685

Lys Asn Asp Ser Leu Cys Ser Val Gln Arg Tyr Val Ile Asn His His
                690                 695                 700

Thr Ser Cys Asn Gly Thr Trp Ser Glu Asp Val Gly Asn His Thr Lys
705                 710                 715                 720

Phe Thr Phe Leu Trp Thr Glu Gln Ala His Thr Val Thr Val Leu Ala
                725                 730                 735

Ile Asn Ser Ile Gly Ala Ser Val Ala Asn Phe Asn Leu Thr Phe Ser
                740                 745                 750

Trp Pro Met Ser Lys Val Asn Ile Val Gln Ser Leu Ser Ala Tyr Pro
                755                 760                 765

Leu Asn Ser Ser Cys Val Ile Val Ser Trp Ile Leu Ser Pro Ser Asp
                770                 775                 780

Tyr Lys Leu Met Tyr Phe Ile Ile Glu Trp Lys Asn Leu Asn Glu Asp
785                 790                 795                 800

Gly Glu Ile Lys Trp Leu Arg Ile Ser Ser Ser Val Lys Lys Tyr Tyr
                805                 810                 815

Ile His Asp His Phe Ile Pro Ile Glu Lys Tyr Gln Phe Ser Leu Tyr
                820                 825                 830

Pro Ile Phe Met Glu Gly Val Gly Lys Pro Lys Ile Ile Asn Ser Phe
                835                 840                 845

Thr Gln Asp Asp Ile Glu Lys His Gln Ser Asp Ala Gly Leu Tyr Val
                850                 855                 860

Ile Val Pro Val Ile Ile Ser Ser Ser Ile Leu Leu Leu Gly Thr Leu
865                 870                 875                 880

Leu Ile Ser His Gln Arg Met Lys Lys Leu Phe Trp Glu Asp Val Pro
                885                 890                 895

Asn Pro Lys Asn Cys Ser Trp Ala Gln Gly Leu Asn Phe Gln Lys Arg
                900                 905                 910

Thr Asp Ile Leu
        915

<210> SEQ ID NO 5
<211> LENGTH: 3705
<212> TYPE: DNA
<213> ORGANISM: Artificial
```

<220> FEATURE:
<223> OTHER INFORMATION: OBRIucfusion

<400> SEQUENCE: 5

```
atggttcttg ccagctctac caccagcatc cacaccatgc tgctcctgct cctgatgctc      60
ttccacctgg gactccaagc ttcaatctcg gcgcgccagg agcagaagct tatctcggag     120
gaggacctga cgcgttatcc aattactcct tggagattta agttgtcttg catgccacca     180
aattcaacct atgactactt cctttttgcct gctggactct caaagaatac ttcaaattcg    240
aatggacatt atgagacagc tgttgaacct aagtttaatt caagtggtac tcacttttct    300
aacttatcca aaacaacttt ccactgttgc tttcggagtg agcaagatag aaactgctcc    360
ttatgtgcag acaacattga aggaacgaca tttgtttcaa cagtaaattc tttagttttt    420
caacaaatag atgcaaactg aacatacag tgctggctaa aaggagactt aaaattattc     480
atctgttatg tggagtcatt atttaagaat ctattcagga attataacta taaggtccat    540
cttttatatg ttctgcctga agtgttagaa gattcacctc tggttcccca aaaaggcagt    600
tttcagatgg ttcactgcaa ttgcagtgtt catgaatgtt gtgaatgtct tgtgcctgtg    660
ccaacagcca aactcaacga cactctcctt atgtgtttga aaatcacatc tggtggagta    720
attttccggt cacctctaat gtcagttcag cccataaata tggtgaagcc tgatccacca    780
ttaggtttgc atatggaaat cacagatgat ggtaatttaa agatttcttg gtccagccca    840
ccattggtac catttccact tcaatatcaa gtgaaatatt cagagaattc tacaacagtt    900
atcagagaag ctgacaagat tgtctcagct acatccctgc tagtagacag tatacttcct    960
gggtcttcgt atgaggttca ggtgagggc aagagactgg atggcccagg aatctggagt   1020
gactggagta ctcctcgtgt ctttaccaca caagatgtca tatactttcc acctaaaatt   1080
ctgacaagtg ttgggtctaa tgtttctttt cactgcatct ataagaagga aaacaagatt   1140
gttccctcaa aagagattgt ttggtggatg aatttagctg agaaaattcc tcaaagccag   1200
tatgatgttg tgagtgatca tgttagcaaa gttacttttt tcaatctgaa tgaaaccaaa   1260
cctcgaggaa gtttacctga tgcagtg tactgctgca atgaacatga atgccatcat   1320
cgctatgctg aattatatgt gattgatgtc aatatcaata tctcatgtga actgatggg    1380
tacttaacta aaatgacttg cagatggtca accagtacaa tccagtcact tgcggaaagc   1440
actttgcaat tgaggtatca taggagcagc ctttactgtt ctgatattcc atctattcat   1500
cccatatctg agcccaaaga ttgctatttg cagagtgatg gtttttatga atgcattttc   1560
cagccaatct tcctattatc tggctacaca atgtggatta ggatcaatca ctctctaggt   1620
tcacttgact ctccaccaac atgtgtcctt cctgattctg tggtgaagcc actgcctcca   1680
tccagtgtga agcagaaat tactataaac attggattat tgaaaatatc ttgggaaaag   1740
ccagtctttc cagagaataa ccttcaattc cagattcgct atggtttaag tggaaaagaa   1800
gtacaatgga agatgtatga ggtttatgat gcaaaatcaa aatctgtcag tctcccagtt   1860
ccagacttgt gtgcagtcta tgctgttcag gtgcgctgta gaggctaga tggactggga   1920
tattggagta attggagcaa tccagcctac acagttgtca tggatataaa agttcctatg   1980
agaggacctg aattttggag aataattaat ggagatacta tgaaaagga gaaaatgtc    2040
actttacttt ggaagcccct gatgaaaaat gactcattgt gcagtgttca gagatatgtg   2100
ataaaccatc atacttcctg caatggaaca tggtcagaag atgtgggaaa tcacacgaaa   2160
ttcactttcc tgtggacaga gcaagcacat actgttacgg ttctggccat caattcaatt   2220
```

-continued

```
ggtgcttctg ttgcaaattt taatttaacc ttttcatggc ctatgagcaa agtaaatatc  2280
gtgcagtcac tcagtgctta tcctttaaac agcagttgtg tgattgtttc ctggatacta  2340
tcacccagtg attacaagct aatgtatttt attattgagt ggaaaaatct taatgaagat  2400
ggtgaaataa aatggcttag aatctcttca tctgttaaga agtattatat ccatgatcat  2460
tttatcccca ttgagaagta ccagttcagt ctttacccaa tatttatgga aggagtggga  2520
aaaccaaaga taattaatag tttcactcaa gatgatattg aaaaacacca gagtgatgca  2580
ggtttatatg taattgtgcc agtaattatt tcctcttcca tcttattgct tggaacatta  2640
ttaatatcac accaaagaat gaaaaagcta ttttgggaag atgttccgaa ccccaagaat  2700
tgttcctggg cacaaggact taattttcag aagagaacgg acattctgga tccaccggct  2760
agagccacca tgaccagcaa ggtgtacgac cccgagcaga ggaagaggat gatcaccggc  2820
ccccagtggt gggccaggtg caagcagatg aacgtgctgg acagcttcat caactactac  2880
gacagcgaga agcacgccga gaacgccgtg atcttcctgc acggcaacgc cgctagcagc  2940
tacctgtgga ggcacgtggt gccccacatc gagcccgtgg ccaggtgcat catccccgat  3000
ctgatcggca tgggcaagag cggcaagagc ggcaacggca gctacaggct gctggaccac  3060
tacaagtacc tgaccgcctg gttcgagctc ctgaacctgc ccaagaagat catcttcgtg  3120
ggccacgact ggggcgcctg cctggccttc cactacagct acgagcacca ggacaagatc  3180
aaggccatcg tgcacgccga gagcgtggtg gacgtgatcg agagctggga cgagtggcca  3240
gacatcgagg aggacatcgc cctgatcaag agcgaggagg cgagaagat ggtgctggag  3300
aacaacttct tcgtggagac catgctgccc agcaagatca tgagaaagct ggagcccgag  3360
gagttcgccg cctacctgga gcccttcaag gagaagggcg aggtgagaag acccaccctg  3420
agctggccca gagagatccc cctggtgaag gcggcaagc ccgacgtggt gcagatcgtg  3480
agaaactaca cgcctacct gagagccagc gacgacctgc ccaagatgtt catcgagagc  3540
gaccccggct tcttcagcaa cgccatcgtg gagggcgcca agaagttccc caacaccgag  3600
ttcgtgaagg tgaagggcct gcacttcagc caggaggacg cccccgacga gatgggcaag  3660
tacatcaaga gcttcgtgga gagagtgctg aagaacgagc agtaa           3705
```

<210> SEQ ID NO 6
<211> LENGTH: 1234
<212> TYPE: PRT
<213> ORGANISM: Artificial
<220> FEATURE:
<223> OTHER INFORMATION: OBRIucfusion

<400> SEQUENCE: 6

```
Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Glu Gln Lys Leu Ile Ser Glu Glu Asp Leu Thr Arg Tyr Pro Ile
        35                  40                  45

Thr Pro Trp Arg Phe Lys Leu Ser Cys Met Pro Asn Ser Thr Tyr
    50                  55                  60

Asp Tyr Phe Leu Leu Pro Ala Gly Leu Ser Lys Asn Thr Ser Asn Ser
65                  70                  75                  80

Asn Gly His Tyr Glu Thr Ala Val Glu Pro Lys Phe Asn Ser Ser Gly
                85                  90                  95

Thr His Phe Ser Asn Leu Ser Lys Thr Thr Phe His Cys Cys Phe Arg
```

-continued

```
                100                 105                 110
Ser Glu Gln Asp Arg Asn Cys Ser Leu Cys Ala Asp Asn Ile Glu Gly
            115                 120                 125
Thr Thr Phe Val Ser Thr Val Asn Ser Leu Val Phe Gln Gln Ile Asp
130                 135                 140
Ala Asn Trp Asn Ile Gln Cys Trp Leu Lys Gly Asp Leu Lys Leu Phe
145                 150                 155                 160
Ile Cys Tyr Val Glu Ser Leu Phe Lys Asn Leu Phe Arg Asn Tyr Asn
                165                 170                 175
Tyr Lys Val His Leu Leu Tyr Val Leu Pro Glu Val Leu Glu Asp Ser
            180                 185                 190
Pro Leu Val Pro Gln Lys Gly Ser Phe Gln Met Val His Cys Asn Cys
        195                 200                 205
Ser Val His Glu Cys Cys Glu Cys Leu Val Pro Val Pro Thr Ala Lys
    210                 215                 220
Leu Asn Asp Thr Leu Leu Met Cys Leu Lys Ile Thr Ser Gly Gly Val
225                 230                 235                 240
Ile Phe Arg Ser Pro Leu Met Ser Val Gln Pro Ile Asn Met Val Lys
                245                 250                 255
Pro Asp Pro Pro Leu Gly Leu His Met Glu Ile Thr Asp Asp Gly Asn
            260                 265                 270
Leu Lys Ile Ser Trp Ser Ser Pro Pro Leu Val Pro Phe Pro Leu Gln
        275                 280                 285
Tyr Gln Val Lys Tyr Ser Glu Asn Ser Thr Thr Val Ile Arg Glu Ala
    290                 295                 300
Asp Lys Ile Val Ser Ala Thr Ser Leu Leu Val Asp Ser Ile Leu Pro
305                 310                 315                 320
Gly Ser Ser Tyr Glu Val Gln Val Arg Gly Lys Arg Leu Asp Gly Pro
                325                 330                 335
Gly Ile Trp Ser Asp Trp Ser Thr Pro Arg Val Phe Thr Thr Gln Asp
            340                 345                 350
Val Ile Tyr Phe Pro Pro Lys Ile Leu Thr Ser Val Gly Ser Asn Val
        355                 360                 365
Ser Phe His Cys Ile Tyr Lys Lys Glu Asn Lys Ile Val Pro Ser Lys
    370                 375                 380
Glu Ile Val Trp Trp Met Asn Leu Ala Glu Lys Ile Pro Gln Ser Gln
385                 390                 395                 400
Tyr Asp Val Val Ser Asp His Val Ser Lys Val Thr Phe Phe Asn Leu
                405                 410                 415
Asn Glu Thr Lys Pro Arg Gly Lys Phe Thr Tyr Asp Ala Val Tyr Cys
            420                 425                 430
Cys Asn Glu His Glu Cys His His Arg Tyr Ala Glu Leu Tyr Val Ile
        435                 440                 445
Asp Val Asn Ile Asn Ile Ser Cys Glu Thr Asp Gly Tyr Leu Thr Lys
    450                 455                 460
Met Thr Cys Arg Trp Ser Thr Ser Thr Ile Gln Ser Leu Ala Glu Ser
465                 470                 475                 480
Thr Leu Gln Leu Arg Tyr His Arg Ser Ser Leu Tyr Cys Ser Asp Ile
                485                 490                 495
Pro Ser Ile His Pro Ile Ser Glu Pro Lys Asp Cys Tyr Leu Gln Ser
            500                 505                 510
Asp Gly Phe Tyr Glu Cys Ile Phe Gln Pro Ile Phe Leu Leu Ser Gly
        515                 520                 525
```

-continued

```
Tyr Thr Met Trp Ile Arg Ile Asn His Ser Leu Gly Ser Leu Asp Ser
    530                 535                 540
Pro Pro Thr Cys Val Leu Pro Asp Ser Val Val Lys Pro Leu Pro Pro
545                 550                 555                 560
Ser Ser Val Lys Ala Glu Ile Thr Ile Asn Ile Gly Leu Leu Lys Ile
                565                 570                 575
Ser Trp Glu Lys Pro Val Phe Pro Glu Asn Asn Leu Gln Phe Gln Ile
            580                 585                 590
Arg Tyr Gly Leu Ser Gly Lys Glu Val Gln Trp Lys Met Tyr Glu Val
        595                 600                 605
Tyr Asp Ala Lys Ser Lys Ser Val Ser Leu Pro Val Pro Asp Leu Cys
    610                 615                 620
Ala Val Tyr Ala Val Gln Val Arg Cys Lys Arg Leu Asp Gly Leu Gly
625                 630                 635                 640
Tyr Trp Ser Asn Trp Ser Asn Pro Ala Tyr Thr Val Val Met Asp Ile
                645                 650                 655
Lys Val Pro Met Arg Gly Pro Glu Phe Trp Arg Ile Ile Asn Gly Asp
            660                 665                 670
Thr Met Lys Lys Glu Lys Asn Val Thr Leu Leu Trp Lys Pro Leu Met
        675                 680                 685
Lys Asn Asp Ser Leu Cys Ser Val Gln Arg Tyr Val Ile Asn His His
    690                 695                 700
Thr Ser Cys Asn Gly Thr Trp Ser Glu Asp Val Gly Asn His Thr Lys
705                 710                 715                 720
Phe Thr Phe Leu Trp Thr Glu Gln Ala His Thr Val Thr Val Leu Ala
                725                 730                 735
Ile Asn Ser Ile Gly Ala Ser Val Ala Asn Phe Asn Leu Thr Phe Ser
            740                 745                 750
Trp Pro Met Ser Lys Val Asn Ile Val Gln Ser Leu Ser Ala Tyr Pro
        755                 760                 765
Leu Asn Ser Ser Cys Val Ile Val Ser Trp Ile Leu Ser Pro Ser Asp
    770                 775                 780
Tyr Lys Leu Met Tyr Phe Ile Ile Glu Trp Lys Asn Leu Asn Glu Asp
785                 790                 795                 800
Gly Glu Ile Lys Trp Leu Arg Ile Ser Ser Ser Val Lys Lys Tyr Tyr
                805                 810                 815
Ile His Asp His Phe Ile Pro Ile Glu Lys Tyr Gln Phe Ser Leu Tyr
            820                 825                 830
Pro Ile Phe Met Glu Gly Val Gly Lys Pro Lys Ile Ile Asn Ser Phe
        835                 840                 845
Thr Gln Asp Asp Ile Glu Lys His Gln Ser Asp Ala Gly Leu Tyr Val
    850                 855                 860
Ile Val Pro Val Ile Ile Ser Ser Ser Ile Leu Leu Leu Gly Thr Leu
865                 870                 875                 880
Leu Ile Ser His Gln Arg Met Lys Lys Leu Phe Trp Glu Asp Val Pro
                885                 890                 895
Asn Pro Lys Asn Cys Ser Trp Ala Gln Gly Leu Asn Phe Gln Lys Arg
            900                 905                 910
Thr Asp Ile Leu Asp Pro Pro Ala Arg Ala Thr Met Thr Ser Lys Val
        915                 920                 925
Tyr Asp Pro Glu Gln Arg Lys Arg Met Ile Thr Gly Pro Gln Trp Trp
    930                 935                 940
```

```
Ala Arg Cys Lys Gln Met Asn Val Leu Asp Ser Phe Ile Asn Tyr Tyr
945                 950                 955                 960

Asp Ser Glu Lys His Ala Glu Asn Ala Val Ile Phe Leu His Gly Asn
                965                 970                 975

Ala Ala Ser Ser Tyr Leu Trp Arg His Val Val Pro His Ile Glu Pro
            980                 985                 990

Val Ala Arg Cys Ile Ile Pro Asp Leu Ile Gly Met Gly Lys Ser Gly
        995                 1000                1005

Lys Ser Gly Asn Gly Ser Tyr Arg Leu Leu Asp His Tyr Lys Tyr
    1010                1015                1020

Leu Thr Ala Trp Phe Glu Leu Leu Asn Leu Pro Lys Lys Ile Ile
    1025                1030                1035

Phe Val Gly His Asp Trp Gly Ala Cys Leu Ala Phe His Tyr Ser
    1040                1045                1050

Tyr Glu His Gln Asp Lys Ile Lys Ala Ile Val His Ala Glu Ser
    1055                1060                1065

Val Val Asp Val Ile Glu Ser Trp Asp Glu Trp Pro Asp Ile Glu
    1070                1075                1080

Glu Asp Ile Ala Leu Ile Lys Ser Glu Glu Gly Glu Lys Met Val
    1085                1090                1095

Leu Glu Asn Asn Phe Phe Val Glu Thr Met Leu Pro Ser Lys Ile
    1100                1105                1110

Met Arg Lys Leu Glu Pro Glu Glu Phe Ala Ala Tyr Leu Glu Pro
    1115                1120                1125

Phe Lys Glu Lys Gly Glu Val Arg Arg Pro Thr Leu Ser Trp Pro
    1130                1135                1140

Arg Glu Ile Pro Leu Val Lys Gly Gly Lys Pro Asp Val Val Gln
    1145                1150                1155

Ile Val Arg Asn Tyr Asn Ala Tyr Leu Arg Ala Ser Asp Asp Leu
    1160                1165                1170

Pro Lys Met Phe Ile Glu Ser Asp Pro Gly Phe Phe Ser Asn Ala
    1175                1180                1185

Ile Val Glu Gly Ala Lys Lys Phe Pro Asn Thr Glu Phe Val Lys
    1190                1195                1200

Val Lys Gly Leu His Phe Ser Gln Glu Asp Ala Pro Asp Glu Met
    1205                1210                1215

Gly Lys Tyr Ile Lys Ser Phe Val Glu Arg Val Leu Lys Asn Glu
    1220                1225                1230

Gln
```

<210> SEQ ID NO 7
<211> LENGTH: 3486
<212> TYPE: DNA
<213> ORGANISM: Artificial
<220> FEATURE:
<223> OTHER INFORMATION: OBRyfpfusion

<400> SEQUENCE: 7

```
atggttcttg ccagctctac caccagcatc cacaccatgc tgctcctgct cctgatgctc    60
ttccacctgg gactccaagc ttcaatctcg gcgcgccagg agcagaagct tatctcggag   120
gaggacctga cgcgttatcc aattactcct tggagattta agttgtcttg catgccacca   180
aattcaacct atgactactt ccttttgcct gctggactct caagaatac ttcaaattcg   240 aatggacatt atgagacagc tgttgaacct aagtttaatt caagtggtac tcacttttct   300
```

-continued

| | | | | |
|---|---|---|---|---|
| aacttatcca | aaacaacttt | ccactgttgc | tttcggagtg | agcaagatag aaactgctcc | 360 |
| ttatgtgcag | acaacattga | aggaacgaca | tttgtttcaa | cagtaaattc tttagttttt | 420 |
| caacaaatag | atgcaaactg | aacatacag | tgctggctaa | aaggagactt aaaattattc | 480 |
| atctgttatg | tggagtcatt | atttaagaat | ctattcagga | attataacta taaggtccat | 540 |
| cttttatatg | ttctgcctga | agtgttagaa | gattcacctc | tggttcccca aaaaggcagt | 600 |
| tttcagatgg | ttcactgcaa | ttgcagtgtt | catgaatgtt | gtgaatgtct tgtgcctgtg | 660 |
| ccaacagcca | aactcaacga | cactctcctt | atgtgtttga | aaatcacatc tggtggagta | 720 |
| attttccggt | cacctctaat | gtcagttcag | cccataaata | tggtgaagcc tgatccacca | 780 |
| ttaggtttgc | atatggaaat | cacagatgat | ggtaatttaa | agatttcttg gtccagccca | 840 |
| ccattggtac | catttccact | tcaatatcaa | gtgaaatatt | cagagaattc tacaacagtt | 900 |
| atcagagaag | ctgacaagat | tgtctcagct | acatccctgc | tagtagacag tatacttcct | 960 |
| gggtcttcgt | atgaggttca | ggtgaggggc | aagagactgg | atgcccagg aatctggagt | 1020 |
| gactggagta | ctcctcgtgt | ctttaccaca | caagatgtca | tatactttcc acctaaaatt | 1080 |
| ctgacaagtt | tgggtctaa | tgtttctttt | cactgcatct | ataagaagga aaacaagatt | 1140 |
| gttccctcaa | aagagattgt | ttggtggatg | aatttagctg | agaaaattcc tcaaagccag | 1200 |
| tatgatgttg | tgagtgatca | tgttagcaaa | gttactttttt | tcaatctgaa tgaaaccaaa | 1260 |
| cctcgaggaa | agtttaccta | tgatgcagtg | tactgctgca | atgaacatga atgccatcat | 1320 |
| cgctatgctg | aattatatgt | gattgatgtc | aatatcaata | tctcatgtga aactgatggg | 1380 |
| tacttaacta | aaatgacttg | cagatggtca | accagtacaa | tccagtcact tgcggaaagc | 1440 |
| actttgcaat | tgaggtatca | taggagcagc | ctttactgtt | ctgatattcc atctattcat | 1500 |
| cccatatctg | agcccaaaga | ttgctatttg | cagagtgatg | gttttttatga atgcattttc | 1560 |
| cagccaatct | tcctattatc | tggctacaca | atgtggatta | ggatcaatca ctctctaggt | 1620 |
| tcacttgact | ctccaccaac | atgtgtcctt | cctgattctg | tggtgaagcc actgcctcca | 1680 |
| tccagtgtga | aagcagaaat | tactataaac | attggattat | tgaaaatatc ttgggaaaag | 1740 |
| ccagtcttc | cagagaataa | ccttcaattc | cagattcgct | atggtttaag tggaaaagaa | 1800 |
| gtacaatgga | agatgtatga | ggtttatgat | gcaaaatcaa | aatctgtcag tctcccagtt | 1860 |
| ccagacttgt | gtgcagtcta | tgctgttcag | gtgcgctgta | agaggctaga tggactggga | 1920 |
| tattggagta | attggagcaa | tccagcctac | acagttgtca | tggatataaa agttcctatg | 1980 |
| agaggacctg | aattttggag | aataattaat | ggagatacta | tgaaaaagga gaaaaatgtc | 2040 |
| actttacttt | ggaagcccct | gatgaaaaat | gactcattgt | gcagtgttca gagatatgtg | 2100 |
| ataaaccatc | atacttcctg | caatggaaca | tggtcagaag | atgtgggaaa tcacacgaaa | 2160 |
| ttcactttcc | tgtggacaga | gcaagcacat | actgttacgg | ttctggccat caattcaatt | 2220 |
| ggtgcttctg | ttgcaaattt | taatttaacc | ttttcatggc | ctatgagcaa agtaaatatc | 2280 |
| gtgcagtcac | tcagtgctta | tcctttaaac | agcagttgtg | tgattgtttc ctggatacta | 2340 |
| tcacccagtg | attacaagct | aatgtatttt | attattgagt | ggaaaaatct taatgaagat | 2400 |
| ggtgaaataa | aatggcttag | aatctcttca | tctgttaaga | agtattatat ccatgatcat | 2460 |
| tttatcccca | ttgagaagta | ccagttcagt | ctttacccaa | tatttatgga aggagtggga | 2520 |
| aaaccaaaga | taattaatag | tttcactcaa | gatgatattg | aaaaacacca gagtgatgca | 2580 |
| ggtttatatg | taattgtgcc | agtaattatt | tcctcttcca | tcttattgct tggaacatta | 2640 |
| ttaatatcac | accaaagaat | gaaaaagcta | ttttgggaag | atgttccgaa cccccaagaat | 2700 |

```
tgttcctggg cacaaggact taattttcag aagagaacgg acattctgga tccaccggtc    2760
gccaccatgg tgagcaaggg cgaggagctg ttcaccgggg tggtgcccat cctggtcgag    2820
ctggacggcg acgtaaacgg ccacaagttc agcgtgtccg gcgagggcga gggcgatgcc    2880
acctacggca agctgaccct gaagttcatc tgcaccaccg gcaagctgcc cgtgccctgg    2940
cccaccctcg tgaccacctt cggctacggc gtgcagtgct tcgcccgcta ccccgaccac    3000
atgcgccagc acgacttctt caagtccgcc atgcccgaag ctacgtcca ggagcgcacc    3060 atcttcttca aggacgacgg caactacaag cccgcgccg aggtgaagtt cgagggcgac    3120
accctggtga accgcatcga gctgaagggc atcgacttca aggaggacgg caacatcctg    3180
gggcacaagc tggagtacaa ctacaacagc acaacgtct atatcatggc cgacaagcag    3240
aagaacggca tcaaggtgaa cttcaagatc cgccacaaca tcgaggacgg cagcgtgcag    3300
ctcgccgacc actaccagca gaacaccccc atcggcgacg gccccgtgct gctgcccgac    3360
aaccactacc tgagctacca gtccgccctg agcaaagacc ccaacgagaa gcgcgatcac    3420
atggtcctgc tggagttcgt gaccgccgcc gggatcactc tcggcatgga cgagctgtac    3480
aagtaa                                                               3486
```

<210> SEQ ID NO 8
<211> LENGTH: 1161
<212> TYPE: PRT
<213> ORGANISM: Artificial
<220> FEATURE:
<223> OTHER INFORMATION: OBRyfbpfusion

<400> SEQUENCE: 8

```
Met Val Leu Ala Ser Ser Thr Thr Ser Ile His Thr Met Leu Leu Leu
 1               5                  10                  15

Leu Leu Met Leu Phe His Leu Gly Leu Gln Ala Ser Ile Ser Ala Arg
                20                  25                  30

Gln Glu Gln Lys Leu Ile Ser Glu Glu Asp Leu Thr Arg Tyr Pro Ile
        35                  40                  45

Thr Pro Trp Arg Phe Lys Leu Ser Cys Met Pro Pro Asn Ser Thr Tyr
    50                  55                  60

Asp Tyr Phe Leu Leu Pro Ala Gly Leu Ser Lys Asn Thr Ser Asn Ser
65                  70                  75                  80

Asn Gly His Tyr Glu Thr Ala Val Glu Pro Lys Phe Asn Ser Ser Gly
                85                  90                  95

Thr His Phe Ser Asn Leu Ser Lys Thr Thr Phe His Cys Cys Phe Arg
                100                 105                 110

Ser Glu Gln Asp Arg Asn Cys Ser Leu Cys Ala Asp Asn Ile Glu Gly
            115                 120                 125

Thr Thr Phe Val Ser Thr Val Asn Ser Leu Val Phe Gln Gln Ile Asp
        130                 135                 140

Ala Asn Trp Asn Ile Gln Cys Trp Leu Lys Gly Asp Leu Lys Leu Phe
145                 150                 155                 160

Ile Cys Tyr Val Glu Ser Leu Phe Lys Asn Leu Phe Arg Asn Tyr Asn
                165                 170                 175

Tyr Lys Val His Leu Leu Tyr Val Leu Pro Glu Val Leu Glu Asp Ser
            180                 185                 190

Pro Leu Val Pro Gln Lys Gly Ser Phe Gln Met Val His Cys Asn Cys
        195                 200                 205

Ser Val His Glu Cys Cys Glu Cys Leu Val Pro Val Pro Thr Ala Lys
```

-continued

```
            210                 215                 220
Leu Asn Asp Thr Leu Leu Met Cys Leu Lys Ile Thr Ser Gly Gly Val
225                 230                 235                 240

Ile Phe Arg Ser Pro Leu Met Ser Val Gln Pro Ile Asn Met Val Lys
                245                 250                 255

Pro Asp Pro Pro Leu Gly Leu His Met Glu Ile Thr Asp Asp Gly Asn
                260                 265                 270

Leu Lys Ile Ser Trp Ser Ser Pro Leu Val Pro Phe Pro Leu Gln
            275                 280                 285

Tyr Gln Val Lys Tyr Ser Glu Asn Ser Thr Thr Val Ile Arg Glu Ala
290                 295                 300

Asp Lys Ile Val Ser Ala Thr Ser Leu Leu Val Asp Ser Ile Leu Pro
305                 310                 315                 320

Gly Ser Ser Tyr Glu Val Gln Val Arg Gly Lys Arg Leu Asp Gly Pro
                325                 330                 335

Gly Ile Trp Ser Asp Trp Ser Thr Pro Arg Val Phe Thr Thr Gln Asp
                340                 345                 350

Val Ile Tyr Phe Pro Pro Lys Ile Leu Thr Ser Val Gly Ser Asn Val
                355                 360                 365

Ser Phe His Cys Ile Tyr Lys Lys Glu Asn Lys Ile Val Pro Ser Lys
        370                 375                 380

Glu Ile Val Trp Trp Met Asn Leu Ala Glu Lys Ile Pro Gln Ser Gln
385                 390                 395                 400

Tyr Asp Val Val Ser Asp His Val Ser Lys Val Thr Phe Phe Asn Leu
                405                 410                 415

Asn Glu Thr Lys Pro Arg Gly Lys Phe Thr Tyr Asp Ala Val Tyr Cys
                420                 425                 430

Cys Asn Glu His Glu Cys His His Arg Tyr Ala Glu Leu Tyr Val Ile
            435                 440                 445

Asp Val Asn Ile Asn Ile Ser Cys Glu Thr Asp Gly Tyr Leu Thr Lys
            450                 455                 460

Met Thr Cys Arg Trp Ser Thr Ser Thr Ile Gln Ser Leu Ala Glu Ser
465                 470                 475                 480

Thr Leu Gln Leu Arg Tyr His Arg Ser Ser Leu Tyr Cys Ser Asp Ile
                485                 490                 495

Pro Ser Ile His Pro Ile Ser Glu Pro Lys Asp Cys Tyr Leu Gln Ser
            500                 505                 510

Asp Gly Phe Tyr Glu Cys Ile Phe Gln Pro Ile Phe Leu Leu Ser Gly
            515                 520                 525

Tyr Thr Met Trp Ile Arg Ile Asn His Ser Leu Gly Ser Leu Asp Ser
530                 535                 540

Pro Pro Thr Cys Val Leu Pro Asp Ser Val Val Lys Pro Leu Pro Pro
545                 550                 555                 560

Ser Ser Val Lys Ala Glu Ile Thr Ile Asn Ile Gly Leu Leu Lys Ile
                565                 570                 575

Ser Trp Glu Lys Pro Val Phe Pro Glu Asn Asn Leu Gln Phe Gln Ile
            580                 585                 590

Arg Tyr Gly Leu Ser Gly Lys Glu Val Gln Trp Lys Met Tyr Glu Val
            595                 600                 605

Tyr Asp Ala Lys Ser Lys Ser Val Ser Leu Pro Val Pro Asp Leu Cys
            610                 615                 620

Ala Val Tyr Ala Val Gln Val Arg Cys Lys Arg Leu Asp Gly Leu Gly
625                 630                 635                 640
```

-continued

Tyr Trp Ser Asn Trp Ser Asn Pro Ala Tyr Thr Val Val Met Asp Ile
            645                 650                 655

Lys Val Pro Met Arg Gly Pro Glu Phe Trp Arg Ile Ile Asn Gly Asp
        660                 665                 670

Thr Met Lys Lys Glu Lys Asn Val Thr Leu Leu Trp Lys Pro Leu Met
    675                 680                 685

Lys Asn Asp Ser Leu Cys Ser Val Gln Arg Tyr Val Ile Asn His His
690                 695                 700

Thr Ser Cys Asn Gly Thr Trp Ser Glu Asp Val Gly Asn His Thr Lys
705                 710                 715                 720

Phe Thr Phe Leu Trp Thr Glu Gln Ala His Thr Val Thr Val Leu Ala
                725                 730                 735

Ile Asn Ser Ile Gly Ala Ser Val Ala Asn Phe Asn Leu Thr Phe Ser
            740                 745                 750

Trp Pro Met Ser Lys Val Asn Ile Val Gln Ser Leu Ser Ala Tyr Pro
        755                 760                 765

Leu Asn Ser Ser Cys Val Ile Val Ser Trp Ile Leu Ser Pro Ser Asp
770                 775                 780

Tyr Lys Leu Met Tyr Phe Ile Ile Glu Trp Lys Asn Leu Asn Glu Asp
785                 790                 795                 800

Gly Glu Ile Lys Trp Leu Arg Ile Ser Ser Ser Val Lys Lys Tyr Tyr
                805                 810                 815

Ile His Asp His Phe Ile Pro Ile Glu Lys Tyr Gln Phe Ser Leu Tyr
            820                 825                 830

Pro Ile Phe Met Glu Gly Val Gly Lys Pro Lys Ile Ile Asn Ser Phe
        835                 840                 845

Thr Gln Asp Asp Ile Glu Lys His Gln Ser Asp Ala Gly Leu Tyr Val
    850                 855                 860

Ile Val Pro Val Ile Ile Ser Ser Ser Ile Leu Leu Leu Gly Thr Leu
865                 870                 875                 880

Leu Ile Ser His Gln Arg Met Lys Lys Leu Phe Trp Glu Asp Val Pro
                885                 890                 895

Asn Pro Lys Asn Cys Ser Trp Ala Gln Gly Leu Asn Phe Gln Lys Arg
            900                 905                 910

Thr Asp Ile Leu Asp Pro Pro Val Ala Thr Met Val Ser Lys Gly Glu
        915                 920                 925

Glu Leu Phe Thr Gly Val Val Pro Ile Leu Val Glu Leu Asp Gly Asp
    930                 935                 940

Val Asn Gly His Lys Phe Ser Val Ser Gly Glu Gly Glu Gly Asp Ala
945                 950                 955                 960

Thr Tyr Gly Lys Leu Thr Leu Lys Phe Ile Cys Thr Thr Gly Lys Leu
                965                 970                 975

Pro Val Pro Trp Pro Thr Leu Val Thr Thr Phe Gly Tyr Gly Val Gln
            980                 985                 990

Cys Phe Ala Arg Tyr Pro Asp His Met Arg Gln His Asp Phe Phe Lys
        995                1000                1005

Ser Ala Met Pro Glu Gly Tyr Val Gln Glu Arg Thr Ile Phe Phe
    1010                1015                1020

Lys Asp Asp Gly Asn Tyr Lys Thr Arg Ala Glu Val Lys Phe Glu
    1025                1030                1035

Gly Asp Thr Leu Val Asn Arg Ile Glu Leu Lys Gly Ile Asp Phe
    1040                1045                1050

```
                                    -continued

Lys  Glu  Asp Gly Asn Ile Leu  Gly His Lys Leu  Glu  Tyr Asn Tyr
     1055                1060                  1065

Asn  Ser  His Asn Val Tyr Ile  Met Ala Asp Lys  Gln  Lys Asn Gly
     1070                1075                  1080

Ile  Lys  Val Asn Phe Lys Ile  Arg His Asn Ile  Glu  Asp Gly Ser
     1085                1090                  1095

Val  Gln  Leu Ala Asp His Tyr  Gln Gln Asn Thr  Pro  Ile Gly Asp
     1100                1105                  1110

Gly  Pro  Val Leu Leu Pro Asp  Asn His Tyr Leu  Ser  Tyr Gln Ser
     1115                1120                  1125

Ala  Leu  Ser Lys Asp Pro Asn  Glu Lys Arg Asp  His  Met Val Leu
     1130                1135                  1140

Leu  Glu  Phe Val Thr Ala Ala  Gly Ile Thr Leu  Gly  Met Asp Glu
     1145                1150                  1155

Leu  Tyr  Lys
     1160
```

METHOD FOR DETECTING LEPTIN RECEPTOR LIGANDS

The present invention relates to a method for detecting leptin receptor ligands using the energy transfer between fusion proteins composed of leptin receptors and of energy-donor or energy-acceptor proteins.

It also relates to fusion proteins for implementing this method.

Leptin is a protein having a molecular weight of 16 kDa which is secreted by adipocytes. This protein is associated with the feeling of satiety, and plays a major role in the control of body weight, energy consumption, bone formation and angiogenesis, but also in other physiological functions, such as the triggering of puberty and the control of reproduction, or the regulation of the T-lymphocyte-mediated immune response.

The leptin receptor (OBR) belongs to the family of cytokine receptors. It is composed, as illustrated in FIG. 1, of a single polypeptide chain comprising a transmembrane domain (Tartaglia et al., J. Biol. Chem., 272, 6093–6096, 1995). Patent application WO 97/19952 relates to this receptor.

Six different isoforms of the OBR, having C-terminal domains with different lengths, have been described. These isoforms all derive from a single gene, by alternative splicing. There also exists a soluble form of OBR containing the leptin-binding site, which corresponds to the extracellular domain of the membrane-bound form. This soluble form, generated post-translationally by proteolysis at the plasma membrane from the membrane-bound forms, is found in the blood. Another soluble form of the OBR, resulting from a mutation generating a stop codon before the transmembrane domain, is also found is certain very rare cases.

A fusion protein consisting of the long form of the leptin receptor (OBR1) fused to EGFP (Enhanced Green Fluorescence Protein) has been used by Lundin et al. (Biochemica and Biophysica Acta, 1499, 130–138, 2000) to study the location of the receptor.

Activation of the OBR is thought to take place via a tetrameric complex composed of two janus kinases 2 (JAK2) and two OBR. Leptin-induced activation of the receptor will induce a change in the conformation of the OBR, which would itself activate a JAK2, which in turn would trans-phosphorylate another JAK2 and then the OBR receptor.

Activation of the OBR appears to be responsible for all the known effects of leptin, such as weight loss, and all the phenomena involved in weight disorders. The inhibitory properties of leptin with respect to bone synthesis have thus recently been demonstrated. Leptin acts by inhibiting the activity of osteoblasts, a population of cells responsible for the formation of bones.

Modifying leptinemia might make it possible to treat diseases associated with a decrease in bone density, such as, for example, osteoporosis, or, conversely, those associated with considerable calcification. In 1999, Xu et al. (Proc. Natl. Acad. Sci. USA 96, 151–156) described a method for detecting protein-protein interactions in living cells. This method is also the subject of patent application WO 99/66324.

This method, called BRET (for Bioluminescent Resonance Energy Transfer) is based on a natural phenomenon, the emission of fluorescence by marine organisms. The enzymatic transformation, by *Renilla* luciferase (Luc), of a substrate which can cross the membrane generates a bioluminescence which, in turn, excites an energy acceptor such as yellow fluorescent protein (YFP). This method corresponds to the LRET (for Luminescent Resonance Energy Transfer) described by Wang et al. (Mol. Gen. Genet. 264: 578–587 (2001)).

The efficiency of the energy transfer depends on the physical proximity and on the respective orientations of the acceptor and of the donor. Thus, the coexpression of luciferase and of YFP is not sufficient to induce an energy transfer since the distance between the two partners must be less than 100 Å. In order to study the interaction between two potential interaction partners, the first protein was fused to luciferase and the second protein to YFP. If the two proteins interact, an energy transfer can be observed.

Since then, the BRET method has been used on a limited number of receptors, having a structure very different from the leptin receptor. Thus, some authors describe the use of the method on receptors of the G protein coupled receptor (GPCR) family, such as the β 2-adrenergic (Angers et al., 2000, Proc. Natl. Acad. Sci. USA 10, 1073), cholesystocine type A (CCK; Cheng et al., 2001, *Biol. Chem.* 276: 48040–48047), and thyrotropin-releasing hormone (Kroeger et al., 2001, *J. Biol. Chem.* 276: 12736–12743) receptors.

These receptors, which are large in size, exhibit a complex structure comprising 7 transmembrane domains. Finally, Boute et al. (2001, *Mol. Pharmacol.* 60: 640–645) have described the following of activation of the insulin receptor using BRET.

The insulin receptor consists of covalent dimers, and not of noncovalent complexes like the leptin receptor. In addition, it comprises quite a long intracellular portion. Finally, the authors show that the change in BRET induced by insulin can only be implemented on the solubilized receptor.

In a few decades, obesity has become a major public health problem in industrialized countries, where it now affects 20 to 30% of the population. These numbers should further increase alarmingly in the years to come. Due to its multifactorial causes, which originate to greater or lesser degrees among, firstly, environmental factors (dietary behavior, access to food, energy expenditure, etc.) and, secondly, multiple genetic causes, obesity constitutes a real challenge for medicine.

Similarly, bone diseases, such as osteoporosis, affect an increasingly large portion of the population. The discovery of novel molecules for treating the various diseases associated with the leptin receptor, such as obesity and osteoporosis, therefore represents high stakes for public health.

However, no method for specifically screening leptin receptor agonists or antagonists exist, which can be used at high throughput.

The applicants have therefore endeavored to implement a rapid, specific and effective screening test for leptin receptor agonists or antagonists.

They have shown, surprisingly, that the change in BRET induced by leptin can be used on one of the isoforms of the leptin receptor, but that it cannot be implemented with all the isoforms.

They have also shown that the implementation of BRET on the leptin receptor is optimal under certain operating conditions.

The present invention therefore relates to a method for detecting leptin receptor ligands using the resonance energy transfer between a first fusion protein composed of a leptin receptor, or of a substantial portion of a leptin receptor, and of an energy donor protein, or of a substantial and active portion of an energy donor protein, and a second fusion protein composed of a leptin receptor, or of a substantial portion of a leptin receptor, and of an energy acceptor protein, or of a substantial and active portion of an energy acceptor protein.

It also relates to fusion proteins for carrying out this method, and also to nucleic acids encoding these proteins.

A subject of the invention is also a method for the curative or preventive treatment of disdeases associated with leptin, consisting in administering a ligand selected using the method defined above to a patient suffering from said disease.

A first subject of the present invention is therefore a fusion protein, which is composed of a leptin receptor, or of a substantial portion of a leptin receptor, and of an energy acceptor or donor protein, or of a substantial and active portion of an energy acceptor or donor protein.

The fusion proteins according to the present invention are composed, in substance, of a portion corresponding to all or part of the sequence of a leptin receptor and of a portion corresponding to an energy donor or acceptor protein. They may, however, comprise other amino acid sequences, derived from other proteins, such as signal sequences. Thus the sequence SEQ ID No. 4 consists of a portion of the sequence SEQ ID No. 2 and of other sequences, and in particular of the signal sequence of mouse interleukin 3.

Advantageously, the energy donor protein is Renilla luciferase. It may, however, be any other energy donor protein, such that the emission spectrum of the donor overlaps sufficiently with the excitation spectrum of the acceptor so as to allow efficient energy transfer between the two parts. It may thus be GFP, if the energy transfer is FRET, or else aequorin if the energy transfer is CRET. Aequorin can be obtained and used as described in patent application EP 0 187 519, or in the article by Inouye et al. (PNAS USA 82: 3154–3158 (1985)).

As regards the energy acceptor fluorescent protein, it is preferentially DsRed, or GFP or a mutant of this protein, such as YFP, EYFP, wild-type GFP, GFPS65T, or Topaz.

It may, however, be any other energy acceptor fluorescent protein, such that the excitation spectrum of the acceptor and the emission spectrum of the donor overlaps sufficiently to allow efficient energy transfer between the two partners.

These proteins are known to those skilled in the art, who can find their sequences in the literature, in particular in the review by Blinks et al. (Pharmacol. Rev. 28: 1–93 (1976)). In particular, GFP is described by Tsien (Annu. Rev. Biochem. 67: 509–544 (1998)) and the cloning thereof is described by Prasher et al. (Gene 111: 229–233 (1992)). As regards the cloning of DsRed, it is described by Matz et al. (Nat. Biotechnol. 17:969–973 (1999)). For Rluc, those skilled in the art can refer to Blinks et al. (Pharmacol. Rev. 28: 1–93 (1976)) or else to Lorenz et al. (PNAS 88: 4438–4442 (1991)).

Advantageously, the isoform of the leptin receptor which is entirely or partly included in the fusion protein is a short isoform, or an isoform exhibiting a short intracellular domain.

Such an isoform advantageously comprises a Box1 intracellular domain, but does not comprise a Box 3 intracellular domain.

Preferentially, this isoform is the OBRs isoform, and even more preferentially the human OBRs isoform. This isoform may, however, come from any other species.

It may also be any other isoform, preferentially short, and even more preferentially comprising at least the extracellular domain of the OBR, such as the soluble form of the OBR containing the leptin-binding site, described by Lee et al. (Nature 379, 632–635 (1996)), Gavrilova et al. (JBC 272: 30546–30551 (1997)), Maamr. et al. (Endocrinology 142: 4389–4393 (2001)) or Clement et al. (Nature 392: 398–401 (1998)).

According to a particularly preferential embodiment, the isoform is the human OBRs isoform of sequence SEQ ID No. 2. It may also be a variant of this protein, exhibiting at least 65%, preferentially at least 75%, and even more preferentially at least 85% or 95%, identity with the sequence SEQ ID No. 2.

The fusion protein may comprise only a portion of the human OBRs isoform. Advantageously it comprises the portion between amino acids 46 and 866 of the sequence SEQ ID No. 2.

The portion corresponding to the leptin receptor may thus have the sequence SEQ ID No. 4, or a variant of this sequence exhibiting at least 65%, preferentially at least 75%, and even more preferentially at least 85% or 95%, identity.

Particularly advantageously, the donor fusion protein has the sequence SEQ ID No. 6, or a variant of this sequence exhibiting at least 65% identity.

Particularly advantageously, the acceptor fusion protein has the sequence SEQ ID No. 8, or a variant of this sequence exhibiting at least 65% identity.

Other subjects of the present invention are nucleic acids encoding these proteins. Such nucleic acids may be complementary or genomic DNAs, or RNAs. These nucleic acids or polynucleotides may be in single-stranded form or in the form of a duplex.

They are particularly advantageously complementary DNAs.

Preferentially, a subject of the invention is a nucleic acid having at least 65%, preferentially at least 75%, and even more preferentially at least 85% or 95%, nucleotide identity with a nucleic acid of sequence SEQ ID No. 5 or SEQ ID No. 7.

According to yet another aspect, the invention relates to a nucleic acid which hybridizes, under high stringency hybridization conditions, with a nucleic acid as defined above, and more particularly a nucleic acid of nucleotide sequences SEQ ID No. 5 and SEQ ID No. 7, or a nucleic acid of complementary sequence.

For the purpose of the present invention, the "percentage identity" between two nucleotide or amino acid sequences can be determined by comparing two optimally aligned sequences through a window of comparison.

The portion of the nucleotide or polypeptide sequence in the window of comparison can thus comprise additions or deletions (for example gaps) relative to the reference sequence (which does not comprise these additions or these deletions) so as to obtain optimal alignment of the two sequences.

The percentage is calculated by determining the number of positions at which an identical nucleic acid base or amino acid residue is observed for the two (nucleic acid or peptide) sequences compared, then dividing the number of positions at which there is identity between the two bases or amino acid residues by the total number of positions in the window of comparison, then multiplying the result by 100 in order to obtain the percentage sequence identity.

The optimal alignment of the sequences for the comparison can be carried out on a computer using known algorithms contained in the WISCONSIN GENETICS SOFTWARE PACKAGE, GENETICS COMPUTER GROUP (GCG), 575 Science Drive, Madison, Wis.

By way of illustration, the percentage sequence identity may be effected using the BLAST program (versions BLAST 1.4.9 of March 1996, BLAST 2.0.4 of February 1998 and BLAST 2.0.6 of September 1998), using exclusively the default parameters (S. F. Altschul et al., J. Mol. Biol. 1990 215: 403–410, S. F. Altschul et al., Nucleic Acids Res. 1997 25: 3389–3402). Blast searches for sequences similar/homologous to a reference "request" sequence, using the algorithm of Altschul et al. The request sequence and the databases used may be peptide- or nucleic acid-related, any combination being possible.

For the purpose of the present invention, the expression "high stringency hybridization conditions" will be intended to mean the following conditions:

1—Membrane Competition and Prehybridization:
  40 µl of salmon sperm DNA (10 mg/ml)+40 µl of human placental DNA (10 mg/ml) are mixed.
  The mixture is denatured for 5 min at 96° C., and then immersed in ice.
  The 2×SSC is removed and 4 ml of formamide mix are poured into the hybridization tube containing the membranes.
  The mixture of the two denatured DNAs is added.
  Incubation is carried out at 42° C. for 5 to 6 hours, with rotation.

2—Labeled Probe Competition:
  10 to 50 µl of Cot I DNA, depending on the amount of repetitions, are added to the labeled and purified probe.
  Denaturation is carried out for 7 to 10 min at 95° C.
  Incubation is carried out at 65° C. for 2 to 5 hours.

3—Hybridization:
  The prehybridization mix is removed.
  40 µl of salmon sperm DNA+40 µl of human placental DNA are mixed; the mixture is denatured for 5 min at 96° C., and then immersed in ice.
  4 ml of formamide mix, the mixture of the two DNAs and the denatured labeled probe/Cot I DNA are added to the hybridization tube.
  Incubation is carried out for 15 to 20 hours at 42° C., with rotation.

4—Washes:
  One wash is carried out at ambient temperature in 2×SSC, to rinse.
  Two 5-minute washes are carried out at ambient temperature, 2×SSC and 0.1% SDS at 65° C.
  Two 15-minute washes are carried out at 65° C., 1×SSC and 0.1% SDS at 65° C.
  The membranes are wrapped in Saran wrap and exposed.

The hybridization conditions described above are suitable for the hybridization under high stringency conditions of a nucleic acid molecule of variable length of 20 nucleotides for several hundred nucleotides.

It goes without saying that the hybridization conditions described above can be adjusted as a function of the length of the nucleic acid the hybridization of which is sought, or of the type of labeling chosen, according to techniques known to those skilled in the art.

The suitable hybridization conditions may, for example, be adjusted according to the teaching contained in the work by HAMES and HIGGINS (1985, "Nucleic acid hybridization: a practical approach", Hames and Higgins Ed., IRL Press, Oxford) or else in the work by F. AUSUBEL et al. (1989, Current Protocols in Molecular Biology, Green Publishing Associates and Wiley Interscience, N.Y.).

The proteins which are the subject of the present invention can be obtained by any means known to those skilled in the art. They are, however, advantageously obtained by expression of the nucleic acids as described above, encoding these proteins, optionally inserted into expression vectors, in advantageously chosen cells, optionally followed by an extraction or a purification which may be total or partial.

The invention also relates to a recombinant vector comprising a nucleic acid according to the invention.

Advantageously, such a recombinant vector will comprise a nucleic acid chosen from the following nucleic acids:

a) a nucleic acid encoding a protein having at least 65% amino acid identity with a sequence SEQ ID No. 6 or SEQ ID No. 8, or a peptide fragment or a variant thereof;

b) a nucleic acid comprising a polynucleotide having a sequence SEQ ID No. 5 or SEQ ID No. 7, or a fragment or a variant thereof;

c) a nucleic acid having at least 65% nucleotide identity with a nucleic acid having a sequence SEQ ID No. 5 or SEQ ID No. 7, or a fragment or a variant thereof;

d) a nucleic acid which hybridizes, under high stringency hybridization conditions, with a nucleic acid of sequence SEQ ID No. 5 or SEQ ID No. 7, or a fragment or a variant thereof.

For the purpose of the present invention, the term "vector" will be intended to mean a circular or linear DNA or RNA molecule which is indifferently in single-stranded or double-stranded form.

According to one embodiment, the expression vector comprises, besides a nucleic acid in accordance with the invention, regulatory sequences for directing the transcription and/or the translation thereof.

According to an advantageous embodiment, a recombinant vector according to the invention will in particular comprise the following elements:

(1) elements for regulating the expression of the nucleic acid to be inserted, such as promoters and enhancers;

(2) the coding sequence included in the nucleic acid in accordance with the invention to be inserted into such a vector, said coding sequence being placed in phase with the regulatory signals described in (1); and (3) suitable transcription initiation and stop sequences.

In addition, the recombinant vectors according to the invention may include one or more origins of replication in the cellular hosts in which their amplification or their expression is desired, markers or selectable markers.

By way of example, the promoters for eukaryotic cells will comprise the HSV virus thymidine kinase promoter or else the mouse metallothionein-L promoter.

In general, for the choice of a suitable promoter, those skilled in the art may advantageously refer to the work by SAMBROOK et al. (1989, "Molecular Cloning: A Laboratory Manual", 2nd ed., Cold Spring Harbor Laboratory Press, Cold Spring Harbor, N.Y.) or else to the techniques described by FULLER et al. (1996, *Immunology in Current Protocols in Molecular Biology*, Ausubel et al.).

The preferred vectors according to the invention are plasmids, such as, for example, vectors pCDNA3 (Invitrogen), pQE70, pQE60, pQE9 (Qiagen), psiX174, pBluescript SA, pNH8A, pNH16A, pNH18A, pNH46A, pWLNEO, pSV2CAT, pOG44, PXTI or pSG (Stratagene).

They may also be vectors of the baculovirus type, such as the vector pVL1392/1392 (Pharmingen) used to transfect cells of the Sf9 line (ATCC No. CRL 1711) derived from *Spodoptera frugiperda*.

They may also be adenoviral vectors, such as human adenovirus type 2 or 5.

A recombinant vector according to the invention may also be a retroviral vector or alternatively an adeno-associated vector (AAV). Such adeno-associated vectors are, for example, described by FLOTTE et al. (1992, *Am. J. Respir. Cell Mol. Biol.*, 7: 349–356).

Subjects of the present invention are also cells comprising a protein, a nucleic acid or a vector as described above, or fragments of these cells, lysates of these cells or else membranes of these cells.

Such cells may be cells isolated from an organism and cultured in an appropriate growth medium. They are, however, preferentially cell lines. Thus, such lines are particularly advantageously the cell lines HEK 293, COS (ATCC No. CRL 1650), COS-M6 and HeLa (ATCC No. CCL2), or else Cv 1 (ATCC No. CC170), Sf-9 (ATCC No. CRL 1711), CHO (ATCC No. CCL-61) or 3T3 (ATCC No. CRL-6361).

The membranes of these cells can be prepared by any method known to those skilled in the art. Preferentially, they will be prepared by mechanical grinding of the cells, and then centrifugation of the suspensions obtained, as illustrated in the examples which follow.

The present invention also relates to compositions comprising cells as described above and saponin.

The present invention also relates to a method for determining the binding of compounds to the leptin receptor, comprising the steps consisting in:
  bringing said compound into contact with an energy donor fusion protein as described above and an energy acceptor fusion protein as described above, or cells, or fragments or lysates or membranes of cells comprising such a protein, and an appropriate enzyme substrate, and
  measuring the energy transfer.

Preferentially, said method is used with cells treated with saponin.

The energy donor fusion proteins and the energy acceptor fusion proteins are chosen such that the energy resulting from the activation of the donor may be transferred efficiently to the acceptor In an advantageous embodiment of said method, the energy donor fusion protein is a protein from fusion between the leptin receptor, or a substantial portion of the leptin receptor, and luciferase, or a substantial portion of luciferase, in which case the substrate is advantageously coelenterazine.

In a preferential embodiment of said method, the energy acceptor fusion protein is a protein from fusion between the leptin receptor, or a substantial portion of the leptin receptor, and YFP, or a substantial portion of YFP.

In an advantageous embodiment of said method, the energy transfer measured in the presence of the test compound is compared to that measured in the absence of the test compound.

Preferentially, the method is used on cell membranes as described above.

Preferentially, the donor and acceptor proteins according to the present invention are chosen such that the energy transfer takes place by BRET or LRET resonance. However, such an energy transfer may be effected by FRET (Fluorescent Resonance Energy Transfer) or else by CRET (Chemiluminescent Resonance Energy Transfer).

Whatever the type of energy transfer, the energy donor fusion protein/energy acceptor fusion protein pairs are chosen so as to allow such a transfer.

CRET consists of energy transfer between aequorin, which is a luciferase, and GFP.

FRET consists of energy transfer between two proteins of the GFP families having different spectra. For the implementation of these transfers, those skilled in the art may refer to Baubet et al. (PNAS USA 97: 7260–7265 (2000)) for CRET, to Matyus (J. Photochem. Photobiol. B 12: 323–337 (1992)) and Pollok and Heim (Trends Cell Biol. 9: 57–60 (1999)) for FRET.

Another subject of the present invention is a method for screening or detecting compounds intended for the prevention and/or treatment of pathological conditions associated with leptin, comprising the steps consisting in:
  bringing said compound into contact with an energy donor fusion protein as described above and an energy acceptor fusion protein as described above, or cells in the absence or presence of saponin, or fragments or lysates or membranes of cells, comprising such proteins, and optionally an appropriate enzyme substrate, and
  measuring the energy transfer.

Such a method may be used for screening leptin receptor agonists or antagonists.

The method according to the present invention is compatible with the 96-well or 384-well plates generally used. It does not require the use of radio-active molecules, is sensitive, reproducible and rapid, and the result is easy to read. Specifically, this method has a good signal/background noise ratio and low cross reactivity with ligands other than leptin. This is explained at least partially by the fact that the activity of the OBR is detected directly at the level of the receptor, which makes it possible to eliminate possible sources of cross reactivity at other levels of the signaling pathways, as can be observed in the case of assays based on reporter genes or on cell growth. In addition, this method is not limited to a transduction pathway having a specific signal, but, on the contrary, is capable of detecting all molecules which interact with the OBR.

This characteristic is particularly advantageous for carrying out large-scale screening, since an increasing number of membrane receptor ligands are found to activate some pathways but not other pathways.

The present invention also relates to the use of compounds selected using a method consisting in:
  bringing said compound into contact with an energy donor fusion protein and an energy acceptor fusion protein as described above, or cells, or fragments or lysates or membranes of cells comprising such a protein, and optionally an appropriate enzyme substrate, and
  measuring the energy transfer, for producing a medicinal product for the curative or preventive treatment of diseases associated with leptin or with its receptor.

Finally, a subject of the invention is a method for the curative or preventive treatment of diseases associated with leptin or with its receptor, comprising the steps of:
  selecting said compound using a method consisting in:
  bringing said compound into contact with an energy donor fusion protein and an energy acceptor fusion protein, or cells, or fragments, lysates or membranes of cells comprising such a protein, and an appropriate enzyme substrate, and
  measuring the energy transfer, and
  of administering said compound to a patient suffering from said disease.

Such diseases may be diseases associated with a decrease in bone density, such as, for example, osteoporosis, or, conversely, those associated with considerable calcification.

They may also be diseases having an effect on weight, such as obesity, diabetes or anorexia. The compounds of the invention may be formulated in pharmaceutical compositions for the purpose of topical, oral, parenteral, intranasal, intravenous, intra-muscular, subcutaneous, intraocular, etc. administration. Preferentially, the pharmaceutical compositions contain pharmaceutically acceptable vehicles for an injectable formulation. They may in particular be salines (monosodium phosphate, disodium phosphate, sodium chloride, potassium chloride, calcium chloride or magnesium chloride, etc., or mixtures of such salts), sterile, isotonic solutions, or dry, in particular lyophilized, compositions which, by addition, as appropriate, of sterilized water or of physiological saline, make it possible to constitute injectable solutes.

Finally, the method according to the present invention also makes it possible to screen serum from obese patients, for the presence or absence of nonfunctional leptin, or else to screen molecules which interfere with the dimerization of the OBR.

FIG. 1 diagrammatically represents the fusion proteins. Box1 represents the JAK2-binding site; Box3 represents the STAT protein-binding site; TM represents the transmembrane domain.

In FIGS. 2a and 2b, the total cell content of OBR and the percentage of cell surface binding sites are respectively measured.

Figure 3:
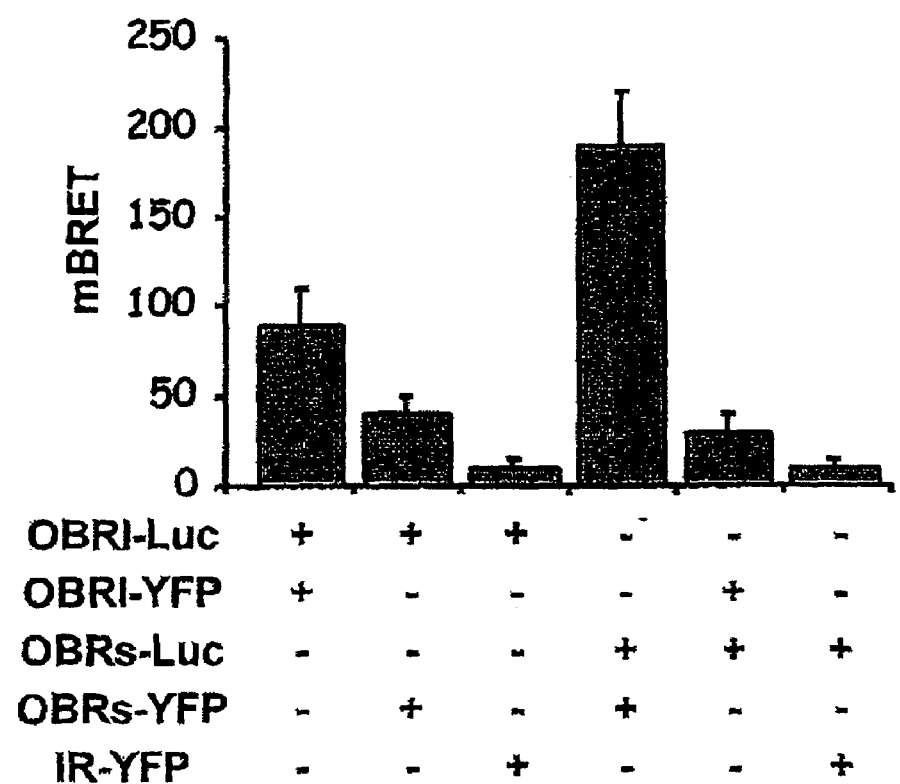

FIG. 3 illustrates the constitutive dimerization of OBR. HEK 293 cells expressing the various OBR constructs indicated are incubated in the presence of coelenterazine. The energy transfer is measured using a luminometer.

Figure 4:
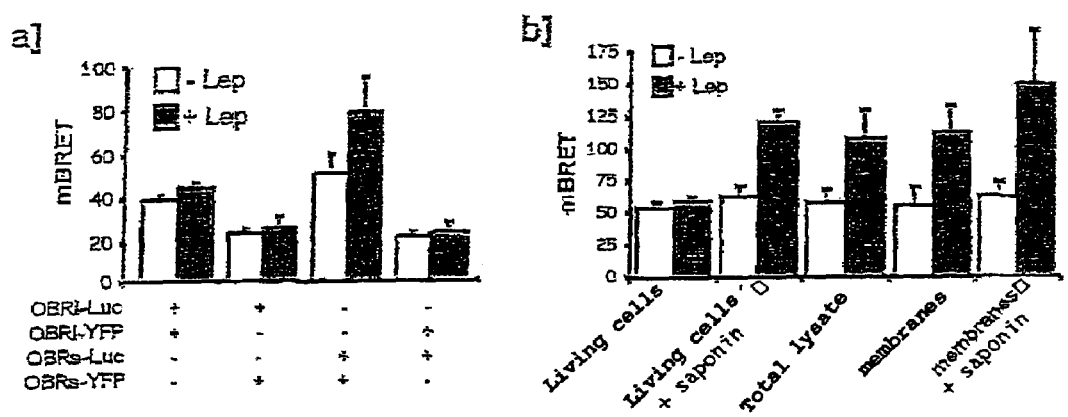

FIGS. 4a and 4b illustrate the effect of leptin binding on the constitutive BRET of the OBR.

FIG. 4a: HeLa cells expressing the various OBR constructs indicated are incubated in the presence of leptin before initiating the luciferase reaction. The energy transfer is measured using a luminometer.

FIG. 4b: The effect of leptin is compared in whole cells coexpressing OBRs-Luc and OBR-YFP, in the presence or absence of saponin, in total lysates and in membrane preparations.

FIGS. 5a to 5e illustrate the optimization and the characterization of the change in BRET induced by leptin on the OBRs. Membranes prepared from HeLa or COS cells coexpressing OBRs-Luc and OBRs-YFP were pre-incubated with or without leptin before initiating the luciferase reaction.

Figure 5:
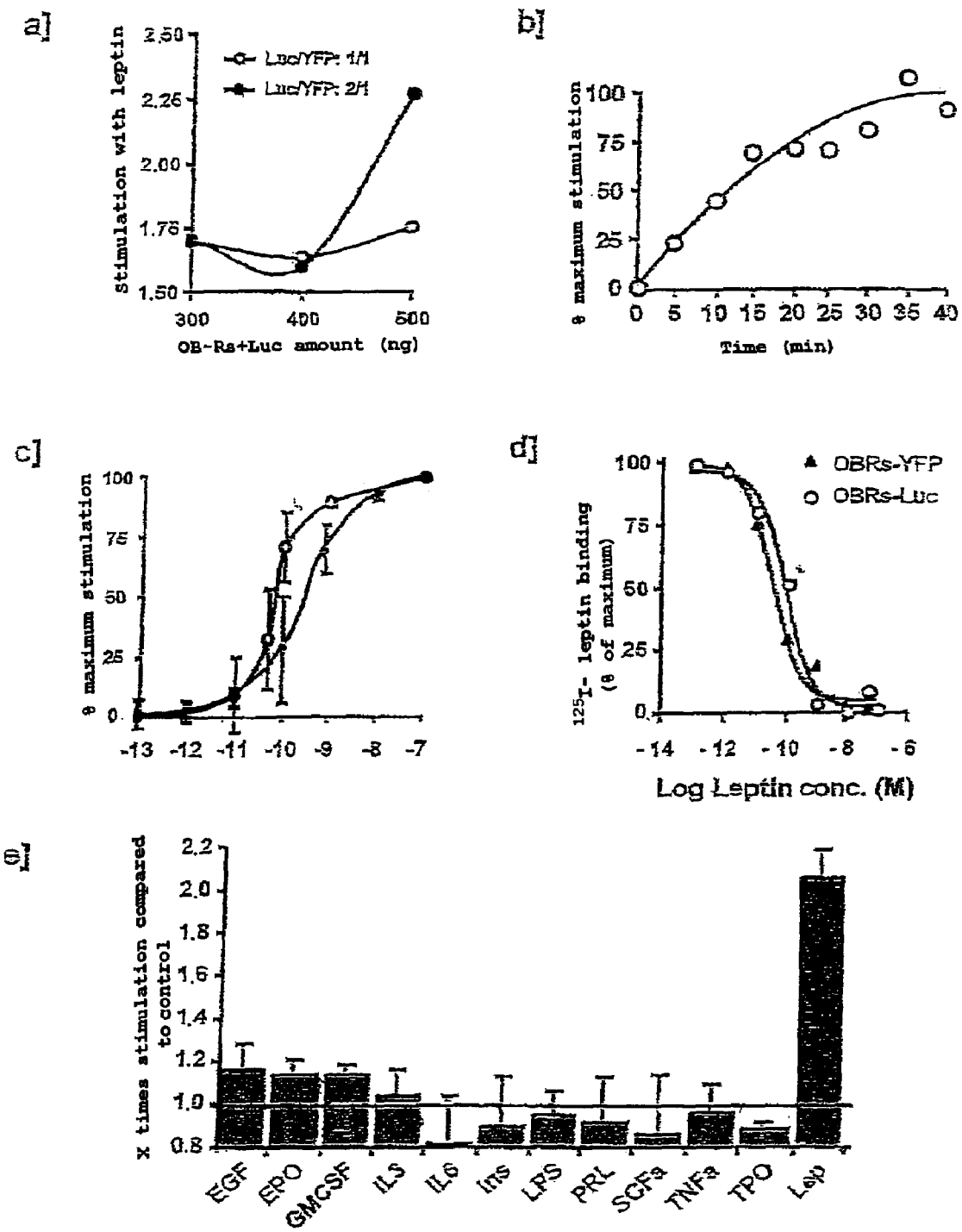

FIG. 5a: Optimization of the relative and absolute levels of expression of OBRs-Luc and of OBRs-YFP.

FIG. 5b: Variation of the BRET signal induced with leptin as a function of time.

FIG. 5c: BRET/leptin concentration dose-response curves on membrane and intact cells in the presence of saponin (0.05%).

FIG. 5d: $^{125}$I-leptin binding competition by augmentation of increasing concentrations of leptin.

FIG. 5e: Specificity of the changes in BRET induced with leptin. The membranes were preincubated with saturating concentrations of erythropoietin (EPO, 10 U/ml), of trombopoietin (TPO, 10 nM), of granulocyte macrophage colony stimulating factor (GM-CSF, 250 ng/ml), of interleukin 3 (IL3, 280 ng/ml), of interleukin 6 (IL6, 100 ng/ml), of prolactin (PRL, 200 ng/ml), of stem cell factor α (SCFα, 250 ng/ml), of epidermal growth factor (EGF, 100 ng/ml), of insulin (Ins, 100 nM), of lipopolysaccharide (LPS, 100 ng/ml) and of tumor necrosis factor α (TNFα, 50 ng/ml).

Figure 6:
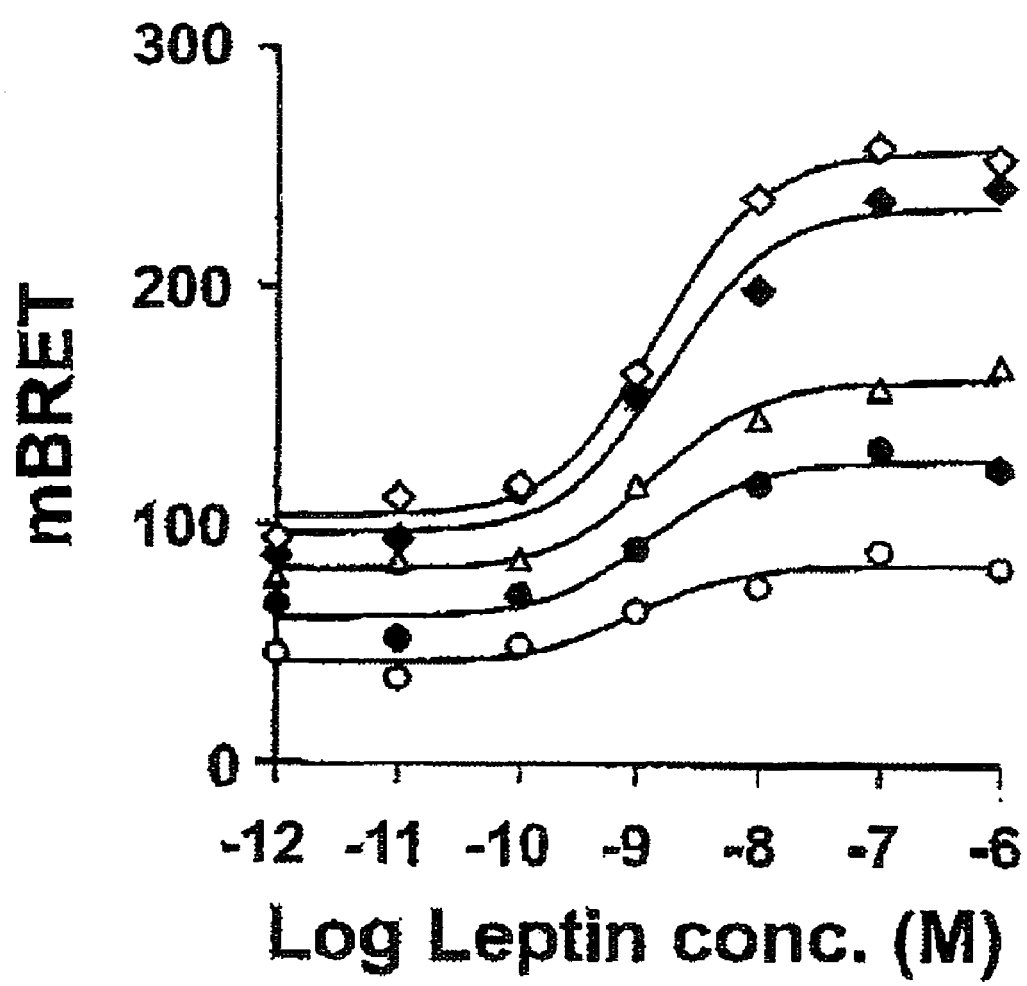

FIG. 6: Cotransfection of COS cells with a constant amount of OB-Rs-Luc (50 ng) and an increasing amount of OB-Rs-YFP: ○, 200 ng; ●, 400 ng; Δ, 800; ♦, 1 600; ◊, 3 200. The BRET measurements were made on the cells in the presence of saponin (0.015%), incubated or not incubated with increasing doses of leptin, and are expressed as mBRET.

The present invention is illustrated, without however being limited, by the following examples.

Materials and Methods Used in the Examples Plasmid Constructs, Transfections and Cell Culture The OB-R-YFP and OB-R-Luc fusion proteins were constructed by ligation of YFP and of Luc to the C-terminal end of the receptors by conventional molecular biology techniques. The coding regions of YFP obtained from the vector pGFPtpz-N1 Cytogem®-Topaze (Packard, Meriden, Conn.) were inserted into the EcoRV site of pcDNA3/CMV (Invitrogen, Groningen, The Netherlands), which contains a modified polylinker site. The coding region of *Renilla* luciferase was obtained from pRL-CMV (Promega, Madison, Wis.) and inserted into the EcoRV site of pcDNA3modified. The coding regions of OBR1 and OBRs (a gift from Dr. Gainsford, Royal Melbourne Hospital, Victoria, Australia) were inserted into the two vectors described above, respectively in the EcoR1/BamH1 and Nhe1 cloning sites. The stop codons were deleted by site-directed mutagenesis and the frame of the fusion protein was adjusted.

The HEK 293, COS-M6 and HeLa cell lines were cultured in DMEM supplemented with the following components: 10% (v/v) FBS, 4.5 g/liter glucose, 100 U/ml penicillin, 0.1 mg/ml streptomycin, 1 mM glutamine (Life Technologies, Gaithersburg, Md.).

The transient transfections were carried out using the FuGene 6 transfection reagent (Roche, Basle, Switzerland).

Fluorescence Microscopy

Two days after transfection with the YFP constructs, the cells were incubated with 100 nM leptin for 60 min and 0.01 mM bisbenzamidine for 15 min before being washed in PBS and fixed for 20 min at ambient temperature in a cold solution of 4% paraformaldehyde in PBS. The sections were observed by fluorescent microscopy using FITC and DAPI filters.

Preparation of Membranes and Solubilization

The cells were placed in ice, washed twice in PBS at the temperature of the ice and detached mechanically in a buffer 1 (5 mM Tris, 2 mM EDTA, pH 7.4, 5 mg/liter of soybean trypsin inhibitor, 5 mg/liter of leupeptin and 10 mg/liter of benzamidine) at the temperature of ice. The cell suspensions are homogenized with a Polytron homogenizer (Janke & Kunkel Ultra-Turrax T25) three times for 5 sec. The lysate is centrifuged at 450×g for 5 min at 4° C. and the supernatant is centrifuged at 48 000×g for 30 min at 4° C. The final pellet is washed twice in buffer 1 and resuspended in a solution (75 mM Tris (pH 7.4), 12.5 mM MgCl$_2$, 5 mM EDTA with protease inhibitors, as described above) and immediately used in radioactive ligand-binding experiments or BRET experiments.

Immunoprecipitation of JAK2

HeLa cells were cotransfected with plasmids expressing JAK2 labeled with HA2 (a gift from Dr. Wojchowski, Pennsylvania State University, Pa. USA) and plasmids containing various OBR constructs. The cells were lysed in lysis buffer (10 mM Tris, 150 mM NaCl, 5 mM EDTA, 5% glycerol, 0.02% $NaN_3$, 0.1% NP40, 1 mM orthovanadate, 5 mg/liter of soybean trypsin inhibitor and 10 mg/liter of benzamidine) and centrifuged for 15 min at 13 000 rpm. The soluble fraction is immuno-precipitated for 2 h with an anti-JAK2 polyclonal antibody (HR-758) (1 µg/ml) (Santa-Cruz Biotechnology, Santa Cruz, Calif.).

SDS-Page Immunoabsorption

The JAK2 immunoprecipitates were denatured in the solution (62.5 mM Tris/HCl (pH 6.8), 5% SDS, 10% glycerol and 0.05% bromophenol blue), at 100° C. for 10 minutes. The proteins were separated by SDS-PAGE in 7% polyacrylamide, and transferred onto nitrocellulose. The immunodetection was carried out with an anti-phosphotyrosine antibody 4G10 (2 µg/ml) (Upstate Biotechnology, Lake Placid, N.Y.). The immunoreactivity was revealed using an appropriate secondary antibody coupled to horseradish peroxidase, and the ECL chemiluminescence agent (Amersham, Aylesbury, UK).

$^{125}$I-leptin-binding Assay

Transfected cells were serum depleted in DMEM (1% BSA) 24 h before the binding experiments. To measure the leptin binding to the surface of the cells, the cells were washed twice with PBS at the temperature of ice and incubated in a binding buffer (DMEM, 25 mM Hepes, pH 7.4, 1% BSA) containing 100 000 cpm/well of $^{125}$I-leptin (Perkin Elmer life sciences, Paris, France) in the presence or absence of 200 nM of nonradioactive leptin (recombinant human leptin (PeproTech Inc., USA)) for 4 h at 4° C. The cells were washed twice with PBS at the temperature of ice, lysed in 1N NaOH and the radioactivity was determined in a gamma-radiation counter. In order to measure the total amount of leptin binding in the extract, the cells were suspended in 1.5 ml of binding buffer containing 0.15% of digitonin for 2 h at 4° C. The extracts were centrifuged for 30 min in an Eppendorf centrifuge at maximum speed, at 4° C. The supernatant (0.2 ml) was incubated with 100 000 cpm of $^{125}$I-leptin in the presence or absence of 200 nM of leptin in a total volume of 0.25 ml, with stirring overnight at 4° C.

0.5 ml of γ-globulin (1.25 mg/ml) and 0.5 ml of polyethylene glycol 6000 (25% w/v) were added in order to precipitate the receptor-ligand complexes, which are obtained by centrifugation (17 000×g for 3 min). The pellet was washed with 1 ml of 12% (w/v) polyethylene glycol 6000, and then counted.

Activation of the Reporter Gene

HeLa cells were cotransfected with 2.6 µg of plasmids carrying the STAT3 reporter gene (a gift from Dr. Levy, New York University, New York, USA), 200 µg of pcDNA3 comprising the coding region of Renilla luciferase (used as internal control) and with 1.4 µg of the various OBR constructs or with the vehicle alone. 48 hours after transfection, the cells were depleted overnight in DMEM (1% BSA) before stimulation with 1 nM of leptin for 6–8 hours. The cells were then washed and lysed in a passive lysis buffer (Promega Corporation, Madison, Wis.) for 15 minutes at ambient temperature. The total lysates were centrifuged for 2 minutes at 15 000 rpm and the supernatants were used in an assay for measuring Luciferase (Promega Corporation, Madison, Wis.) using a Berthold luminometer (Lumat LB 9507). The results are expressed by the ratio of the firefly luciferase/Renilla luciferase activity.

Measurement of BRET 48 hours after transfection, HeLa, COS and HEK 293 cells expressing OBR were detached and washed with PBS. 1-2×10$^5$ cells were distributed into 96-well optical plates (Packard Instrument Company, Meriden, Conn.) in the presence or absence of ligands, at 25° C. Membranes prepared from cells expressing OBR were used for the measurements of BRET. The substrate, coelenterazine h (Molecular Probes, Eugene, Oreg.), was added at a final concentration of 5 µM and the reading was carried out with a Fusion™ fluoro/luminometer (Packard Instrument Company, Meriden, Conn.), which permits the sequential integration of the luminescence signals detected with two filters (Luc filter: 485±10 nm; YFP filter: 530±12.5 nm). The BRET ratio is defined as the difference in the emission at 530 nm/485 nm of the cotransfected Luc and YFP fusion proteins and the emission at 530 nm/485 nm of the Luc fusion protein alone. The results are expressed in milliBRET units (mBU), 1 mBRET unit corresponding to the value of the BRET ratio multiplied by 1 000. The following ligands were used to determine the specificity of the assay: recombinant human erythropoietin (EPO), insulin (Ins), lipopolysaccharide (LPS, Sigma Aldrich, St. Louis, USA), recombinant human trombopoietin (TPO), GM-CSF, interleukin 3 (IL3), interleukin 6 (IL6), prolactin (PRL), SCF, EGF and TNFα.

EXAMPLE 1

Functional Expression of the OBR Fusion Proteins

Figure 1:
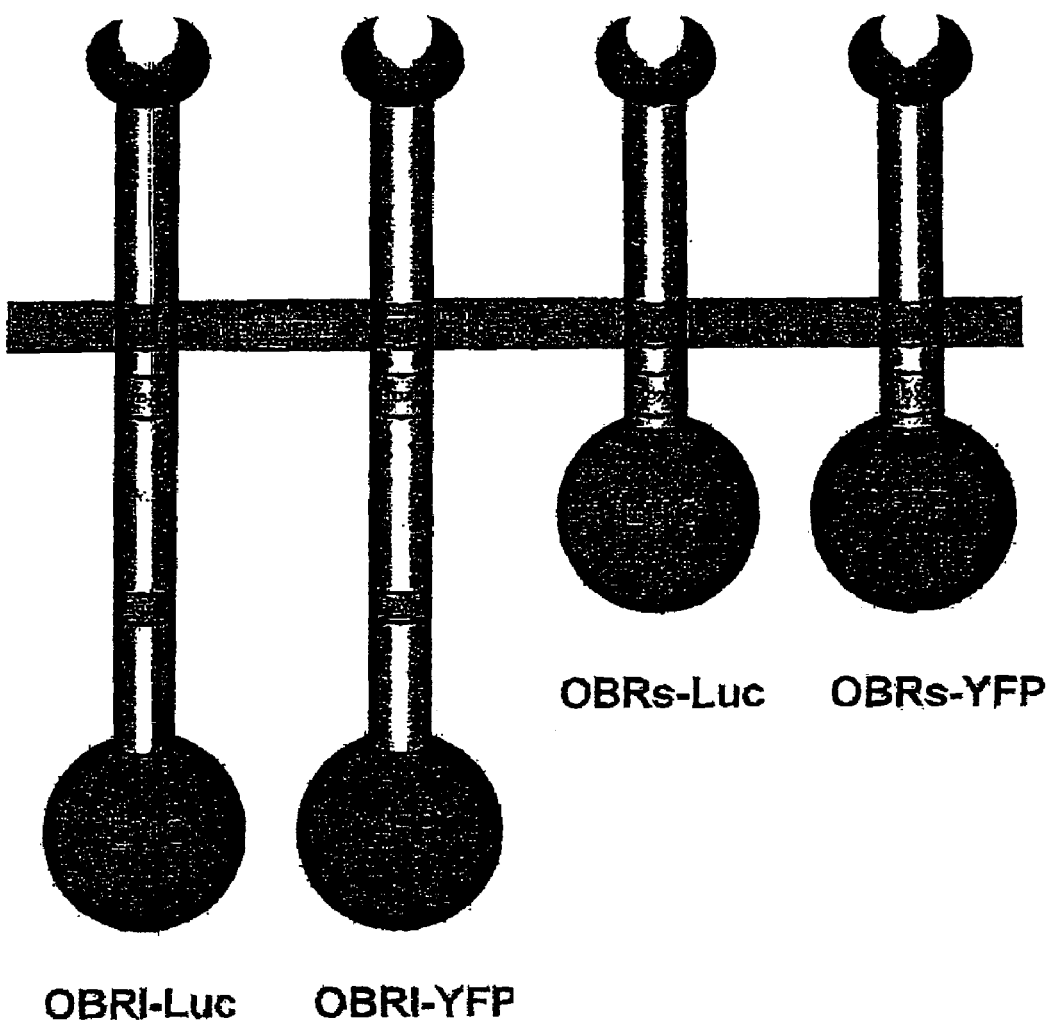
Figure 2:
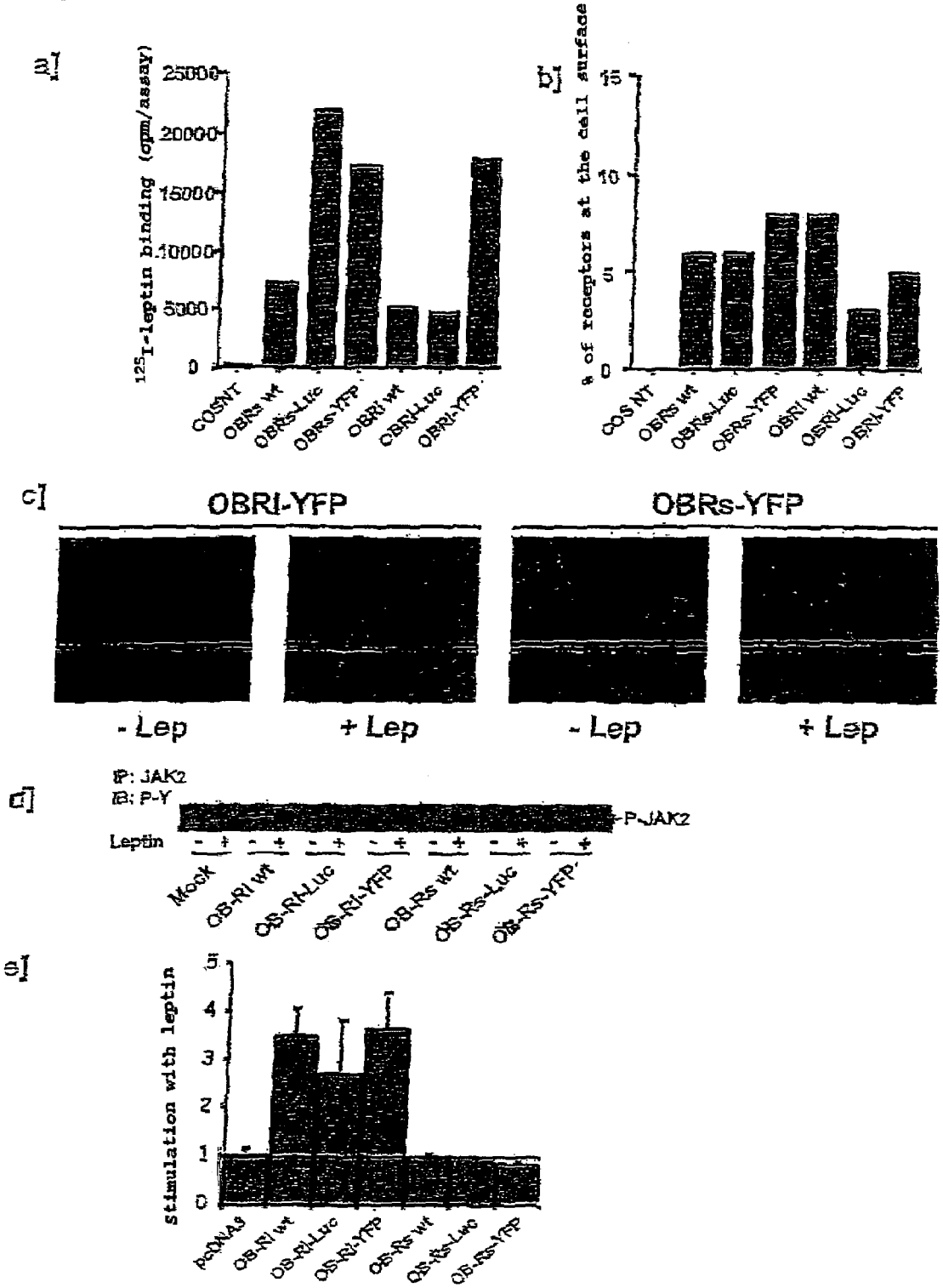
FIGS. 2a and 2b illustrate the expression of the OBR constructs in COS cells, estimated by radio-labeling experiments using $^{125}$I-leptin as radio ligand.
FIG. 2c illustrates the cellular location of the expression of the OBR1-YFP and OBRs-YFP construct in the presence and absence of leptin.
FIG. 2d illustrates the activation of JAK2 with various OBR constructs.
FIG. 2e illustrates the effect of the stimulation with leptin of cells coexpressing the reporter gene for STAT3 and various OBR constructs.

The long form (OBR1) and the short form (OBRs) of the OBR were fused at their C-terminal ends with YFP or Luc (FIG. 1). The expression of these fusion proteins was confirmed in transfected COS cells in binding experiments with $^{125}$I-leptin (FIG. 2a). Similar results were obtained in transfected HeLa cells. The expression, at the surface of the cells, of the fusion proteins and of wild-type receptors expressed in the COS cells vary between 5 and 10%, which is in agreement with already known values. Similar values are obtained in HEK 293 cells expressing endogenous OBR (14 ±3%).

The location of the OBR fusion proteins in the HeLa cells was studied by fluorescence microscopy using the proteins from fusion with YFP. The fluorescence due to OBR1-YFP is distributed in a punctate fashion in the cells whereas that due to OBRS-YFP is located in plaques. Stimulation with leptin localized OBR1-YFP in large intracellular plaques probably corresponding to the endosomal compartment. The location of OBRS-YFP does not change significantly. The results obtained by fluorescence microscopy confirm the predominant location of OBR in the intracellular compartment and are coherent with the already known location of the OBR1-GFP fusion protein in COS cells.

The functional expression of the fusion proteins is evaluated by measuring the activation of the JAK-STAT pathway. The JAK2 kinases are associated with intra-cellular domains of OBRs and OBR1. Ligand binding induces trans-phosphorylation of JAK2 and phosphorylation of OBR1, but not of OBRs. Phosphorylated OBR1 then provides a site attachment for the STAT proteins, which are activated by phosphorylation of the tyrosine after binding to the receptor. The activated STAT proteins then dimerize and are translocated to the nucleus, where they stimulate gene transcription via STAT responsive elements, as described by Tartaglia (1997, J. Biol. Chem. 272, 6093–6096).

As shown in FIG. 2c, all the OBRs constructs induce JAK2 phosphorylation, which indicates activation of JAK2. The activity of the STAT3 reporter gene is activated 2- to 4-fold by OBR1-wt and the OBR1 fusion proteins, whereas the short isoforms have no effect on the activity of the reporter gene. These results indicate that the OBR fusion proteins are functionally expressed in the HeLa cells.

EXAMPLE 2

Constitutive Dimerization of OBR in Living Cells

The dimerization of OBR-Luc and OBR-YFP was studied in living cells.

Significant energy transfers were observed between OBRs-Luc and OBRs-YFP and also between OBR1-Luc and OBR1-YFP, expressed in equimolar amounts, which indicates that constitutive homodimers exist for the two receptors (FIG. 3a, b). The existence of the OBRs/OBR1 hetero dimers in the living cells is demonstrated by the detection of BRET between OBRs-Luc and OBR1-YFP, and also between OBR1-Luc and OBRs-YFP. The specificity of these interactions is illustrated by the absence of significant transfer between OBRs-Luc and OBR1-Luc and a protein from fusion between YFP and the insulin receptor recently described (Boute et al., 2001, mentioned above).

These results indicate that the short and long isoforms are involved in hetero- and homocomplexes in living cells.

EXAMPLE 3

Effect of Leptin Binding on Constitutive BRET of the OBR

In order to evaluate the agonist effects on the constitutive BRET, the cells were preincubated with leptin before initiating the luciferase reaction with its substrate.

No change in the constitutive BRET is observed with the OBR1 homodimers and the two combinations of hetero dimers OBRs/OBR1, whereas the BRET is increased with the OBRs homodimers (FIG. 4a).

The changes in BRET of the OBRs homodimers induced by leptin were then measured in various cell preparations. Mechanical rupture of the cells in a hypotonic buffer significantly enhances the increase in BRET with leptin, whereas the basal BRET remains unchanged. Similar results were obtained with the membrane fraction after separation from the cytosol. While all the OBRs-Luc/OBRs-YFP couples contribute to the basal BRET, only the receptors exposed to the cell surface (5–10%) can be stimulated by leptin, which is impermeable to the membranes in intact cells.

Disruption of the cell membranes increases the OBR fraction which is accessible to leptin and which is responsible for the increase in the BRET induced by leptin.

Similar results were obtained on cells treated with saponin. This component makes holes in the membranes and allows penetration of proteins such as leptin into the intracellular compartments where the majority of the OBR are found.

No change in leptin-induced BRET was observed in similar experiments carried out with preparations using cells expressing OBR1 homodimers—or OBRs/OBR1 heterodimers.

The amounts of and the ratios of OBRs-Luc and OBRs-YFP were then modulated in order to optimize the leptin-induced BRET (FIG. 5a). The best results are obtained when 500 ng of DNA encoding OBRs-Luc and 250 ng of DNA encoding OBRs-YFP are used.

Under these optimized conditions, a saturated concentration of leptin induces a 2- to 2.5-fold increase in the basal BRET signal in cells incubated with saponin or membranes prepared from cells expressing OBRs homodimers. This increase depends on time. The maximum values are reached after 20 minutes of incubation with 1 nM leptin at ambient temperature (FIG. 5b). For higher concentrations of leptin, the maximum values are obtained after 5 minutes of incubation at ambient temperature.

The effect of the leptin is dose-dependent, with an EC50 of approximately 100 pM (FIG. 5c), which is in agreement with the Ki values obtained with the OBRs-Luc (116 pM) and OBRs-YFP (35 pM) fusion proteins (FIG. 5d). The specificity of the assay is demonstrated by the absence of BRET induced by the ligand with a saturating concentration of several cytokines and other membrane receptor ligands, such as erythropoietin, thrombopoietin, GM-CSF, IL3, IL6, PRL, SCF$\alpha$, EGF, insulin, LPS and TNF$\alpha$.

The distribution of the receptors in dimers follows statistical laws, and at a 1/1 receptor number ratio, the following distribution is expected if all the receptors are in dimeric form: 1/4 Luc/Luc, 1/4 YFP/YFP and 1/2 receptors capable of engendering a BRET signal (1/4 Luc/YFP, 1/4 YFP/Luc). However, in the BRET measurements, all of the molecules fused to Luc give a luminescence signal and therefore, at a 1/1 ratio, half the receptors capable of BRET are observed, on a total donor population. Thus, to increase the BRET signal, experiments were carried out in which the Luc molecules were saturated with the YFP molecules so as to have all the Luc molecules in the form of dimers with the YFP molecules (capable of BRET). The results in FIG. 6 show that the basal BRET signal increases during the saturation and that the induction with leptin is proportional to the basal signal, with a 2- to 2.5-fold stimulation of the basal BRET. At saturation, a better resolution of the basal and induced BRET is obtained, allowing easier screening for the search for molecules.

The invention claimed is:

1. A method for determining the binding of a compound to a leptin receptor comprising the steps of:
   i.) bringing said compound into contact with a first fusion protein consisting of a leptin receptor and an energy donor protein, wherein said leptin receptor consists of a short isoform comprising Box1 intracellular domain free of Box 3 intracellular domain or a soluble form of leptin receptor which contains the leptin-binding region of the molecule and said energy donor protein is a luciferase, GFP or aequorin, and a second fusion protein consisting of a leptin receptor and an energy acceptor protein, wherein said leptin receptor consists of a short isoform comprising Box1 intracellular domain free of Box 3 intracellular domain or a soluble form of leptin receptor which contains the leptin-binding region of the molecule and said energy acceptor protein is DsRed, GFP or a mutant of GFP,
   ii.) adding an enzyme substrate when said donor protein is a luciferase or aequorin, and
   iii.) measuring the energy transfer wherein the energy transfer measured in the presence of said compound is compared to that measured in the absence of said compound
   wherein an increase in energy transfer in the presence of said compound compared to that measured in the absence of said compound is indicative of binding of a compound to a leptin receptor.

2. The method of claim 1 wherein said substrate is coelenterazine.

3. The method of claim 1 wherein said first fusion protein is expressed in a first cell and said second fusion protein is expressed in a second cell and said cells are lysed to form cell fragments, cell membranes or cell lysates.

4. The method of claim 3 wherein saponin is added to first and second cell to lyse the cells.

5. A method for screening leptin receptor agonists or antagonists comprising the steps of:
   i.) bringing said compound into contact with a first fusion protein consisting of a leptin receptor and an energy donor protein, wherein said leptin receptor consists of a short isoform comprising Box1 intracellular domain free of Box 3 intracellular domain or a soluble form of leptin receptor which contains the leptin-binding region of the molecule and said energy donor protein is a luciferase, GFP or aequorin, and a second fusion protein consisting of a leptin receptor and an energy acceptor protein, wherein said leptin receptor consists of a short isoform comprising Box1 intracellular domain free of Box 3 intracellular domain or a soluble form of leptin receptor which contains the leptin-binding region of the molecule and said energy acceptor protein is DsRed, GFP or a mutant of GFP,
   ii.) adding an enzyme substrate when said donor protein is a luciferase or aequorin, and
   iii.) measuring the energy transfer wherein the energy transfer measured in the presence of said compound is compared to that measured in the absence of said compound
   wherein a change in energy transfer in the presence of said compound compared to that measured in the absence of said compound is indicative of the compound being a leptin receptor agonist or antagonist.

6. The method of claim 1 or 5 wherein said leptin receptor short isoform comprises the sequence of SEQ ID NO:2.

7. The method of claim 1 or 5 wherein said leptin receptor short isoform comprises the amino acid sequence 46 to 866 of SEQ ID NO:2.

8. The method of claim 1 or 5 wherein said first fusion protein comprises the sequence of SEQ ID NO:6.

9. The method of claim 1 or 5 wherein said second fusion protein comprises the sequence of SEQ ID NO:8.

10. The method of claim 1 or 5 wherein said leptin receptor short isoform comprises the sequence of SEQ ID NO:4.

* * * * *